United States Patent
Michel et al.

(10) Patent No.: US 11,802,108 B2
(45) Date of Patent: Oct. 31, 2023

(54) COMPOUNDS FOR THE MODULATION OF CYCLOPHILINS FUNCTION

(71) Applicant: The University Court of The University of Edinburgh, Edinburgh (GB)

(72) Inventors: Julien Michel, Edinburgh (GB); Alessio De Simone, Edinburgh (GB); Charalampos Ioannidis, Edinburgh (GB); Jordi Juarez-Jimenez, Edinburgh (GB); Charis Georgiou, Edinburgh (GB); Arun Gupta, Edinburgh (GB); Alison Hulme, Edinburgh (GB); Malcolm Walkinshaw, Edinburgh (GB); Dahlia Doughty Shenton, Edinburgh (GB)

(73) Assignee: The University Court of the University of Edinburgh, Edinburgh (GB)

( * ) Notice: Subject to any disclaimer, the term of this patent is extended or adjusted under 35 U.S.C. 154(b) by 0 days.

(21) Appl. No.: 17/269,338

(22) PCT Filed: Aug. 29, 2019

(86) PCT No.: PCT/EP2019/073106
§ 371 (c)(1),
(2) Date: Feb. 18, 2021

(87) PCT Pub. No.: WO2020/043831
PCT Pub. Date: Mar. 5, 2020

(65) Prior Publication Data
US 2021/0238130 A1    Aug. 5, 2021

(30) Foreign Application Priority Data
Aug. 29, 2018  (GB) .................... 1814067

(51) Int. Cl.
*C07C 275/24*      (2006.01)
*C07C 323/60*      (2006.01)
(Continued)

(52) U.S. Cl.
CPC .......... *C07C 275/24* (2013.01); *C07C 323/60* (2013.01); *C07D 207/16* (2013.01);
(Continued)

(58) Field of Classification Search
CPC . C07C 275/24; C07C 323/60; C07C 2601/02; C07C 2601/16; C07D 207/16;
(Continued)

(56) References Cited

U.S. PATENT DOCUMENTS 5,744,621 A * 4/1998 Kim ................. A61P 31/12
546/169

FOREIGN PATENT DOCUMENTS

WO  2011076784 A2  6/2011
WO  2017173048 A1  10/2017
(Continued)

OTHER PUBLICATIONS

CAS Registry No. 1172716-02-7, which entered STN on Aug. 5, 2009 (Year: 2009).*
(Continued)

*Primary Examiner* — Matthew P Coughlin
(74) *Attorney, Agent, or Firm* — Leber IP Law; Shelly M. Fujikawa

(57) ABSTRACT

The present invention relates to compounds of formula (I) or a pharmaceutically acceptable salt thereof useful as inhibitors of Cyclophilins and modulators of cyclophilin-like proteins. The invention also relates to uses of said compounds in the treatment of various disorders. Formula (I), wherein: $R^1$ and $R^2$ are each independently is selected from the group consisting of —R, -haloalkyl, -hydroxyalkyl, —OR, —C(O)R, —CO2R, —C(O)N(R)2, —NRC(O)R, and —N(R)2; wherein $R^2$ could also be a sulphide; each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, sulphur, or a 5-6 membered monocyclic heteroaryl ring having 1-4 heteroatoms selected from nitrogen, oxygen, or sulphur; $R^3$ is Formula (Ia) selected from the group consisting of —OEt, and wherein $R^5$ and $R^6$ are independently selected from the group consisting of H, halide, methoxy, thiomethyl, morpholine and trifluoromethyl; $R^4$ is selected from the group consisting of $C_{1-6}$-alkyl-, and $R^{4.1}$—$CH_2$— wherein, $R^{4.1}$ is $C_{3-6}$-cycloalkyl-, a 5-6 membered heterocyclic ring having 1-4 heteroatoms independently selected from nitrogen, oxygen, sulphur; optionally substituted with one $R^{4.1.1}$ wherein, $R^{4.1.1}$ is selected from —H, $C_{1-4}$-alkyl, optionally substituted with one substituent selected from $H_2N(O)C$— or EtO(O)C—; X is carbon or nitrogen; A is selected from the group consisting of 6 membered unsaturated ring, with 1-3 nitrogen atoms, which is optionally substituted by —$NH_2$, and Formula (Ib), wherein ring B is a fused 5-10 membered saturated or partially unsaturated heterocyclic mono-bicyclic ring having 1-3 heteroatoms selected from nitrogen, oxygen or sulphur, which is optionally substituted by —OH; and m is 1 or 2; and n is 1 or 2.

(I)

(Continued)

-continued (Ia)

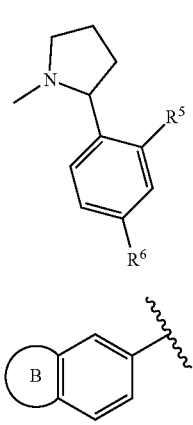

(Ib)

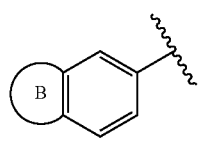

16 Claims, 1 Drawing Sheet

(51) Int. Cl.
  *C07D 207/16* (2006.01)
  *C07D 257/04* (2006.01)
  *C07D 403/12* (2006.01)
  *C07D 491/08* (2006.01)

(52) U.S. Cl.
  CPC ......... *C07D 257/04* (2013.01); *C07D 403/12* (2013.01); *C07D 491/08* (2013.01); *C07C 2601/02* (2017.05); *C07C 2601/16* (2017.05)

(58) Field of Classification Search
  CPC ... C07D 257/04; C07D 403/12; C07D 491/08
  See application file for complete search history.

(56) References Cited

FOREIGN PATENT DOCUMENTS

| | | |
|---|---|---|
| WO | 2017173049 A1 | 10/2017 |
| WO | 2017173052 A1 | 10/2017 |

OTHER PUBLICATIONS

De Simone et al. Chem. Sci. 2019, 10, 542-547 (Year: 2018).*
International Search Report issued on International Application PCT/EP2019/073106, dated Nov. 19, 2019, 6 pages.
Database accession No. m: 1457324-88-7, "C:\EPODAT A \SEA \eplogf\sal 702721.log", Chemical Abstracts Service, Columbus, OH, US, Oct. 13, 2013, 1 page.
Shore et al., "Small Molecule Inhibitors of Cyclophilin D To Protect Mitochondrial Function as a Potential Treatment for Acute Pancreatitis", Journal of Medicinal Chemistry, vol. 59 No. 6, Mar. 7, 2016, pp. 2596-2611.
De Simone et al., "A computationally designed binding mode flip leads to a novel class of potent tri-vector cyclophilin inhibitors", Chemical Science, vol. 10, Oct. 23, 2018, pp. 542-547.
Great Britain Patent Application No. GB1814067.3, Search Report dated Feb. 28, 2019, 5 pages.

* cited by examiner

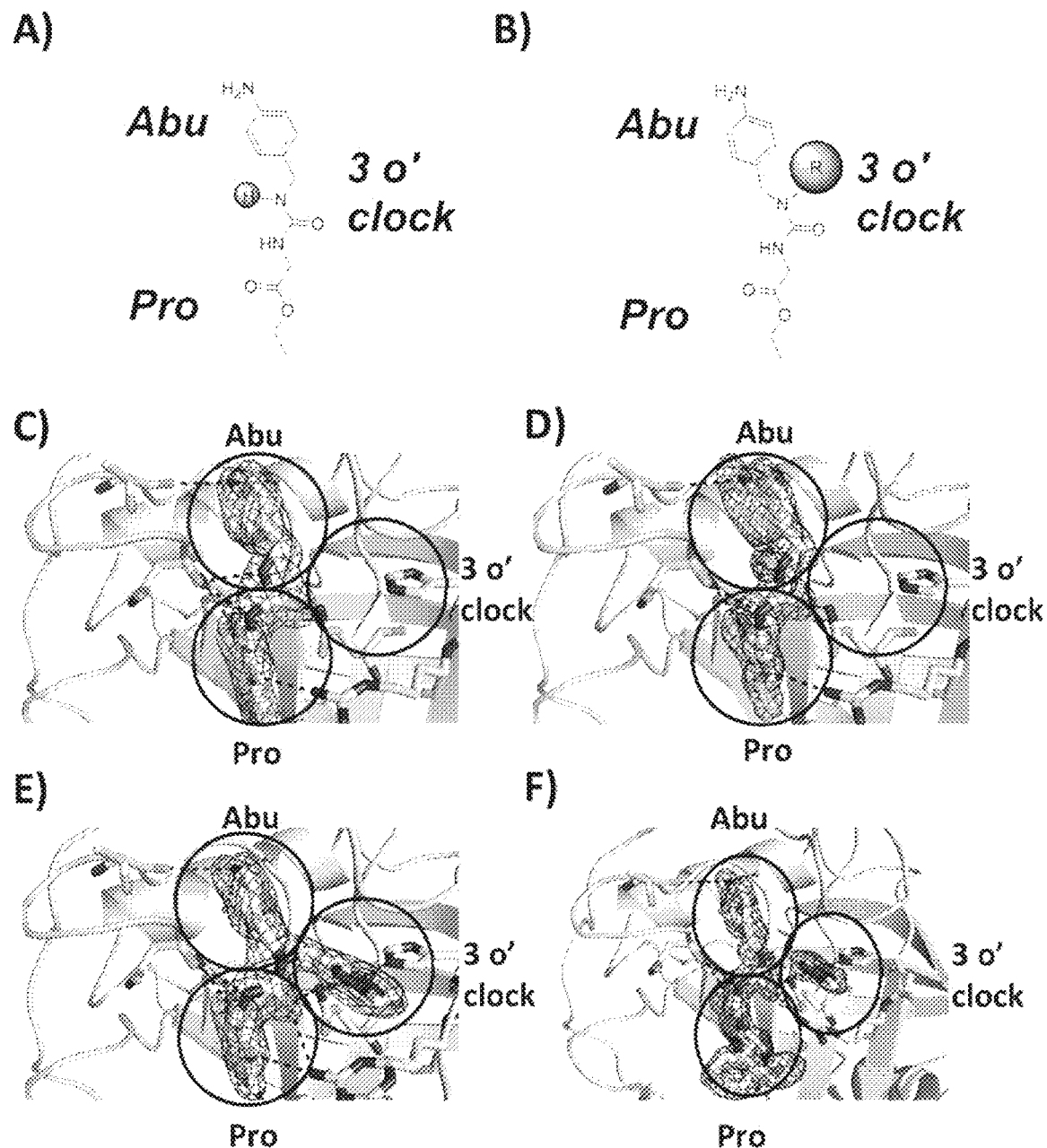

COMPOUNDS FOR THE MODULATION OF CYCLOPHILINS FUNCTION

The present invention relates to compounds useful as inhibitors of Cyclophilins and modulators of cyclophilin-like proteins. The invention also relates to pharmaceutical compositions comprising the compounds and uses of said compounds and compositions in the treatment of various disorders.

BACKGROUND OF THE INVENTION

Cyclophilins (Cyps) are molecular chaperones, belonging to the class of peptidyl prolyl cis-trans isomerases, known to catalyse the isomerization of peptidyl-prolyl amide bonds in unfolded and native proteins.

Cyps play a pivotal role in a multitude of cellular functions such as cell growth, proliferation and motility. There are 7 major Cyp proteins found in humans—CypA, CypB, CypC, CypD, CypE, Cyp40, and CypNK. A total of 17 isoforms are known in humans. The most common variants are CypA, CypB and CypD. They are found predominantly in the endoplasmic reticulum, and CypD localises in mitochondria. CypE is found in the nucleus and Cyp40 and CypNK are found in the cytosol. NKTR, is a membrane-localised receptor with a Cyp domain. Many Cyps (including NKTR) possess a peptidyl-prolyl cis/trans isomerase activity (PPlase). It is thought that Cyps speed up protein folding and also repair damaged proteins. CypA and CypB are also pro-inflammatory cytokines. CypD is a key component of the mitochondrial permeability transition pore.

Cyclophilins are known to be implicated in many diseases and injuries such as viral and parasitic infections, cardiovascular diseases, ischemia/reperfusion injury, diabetes, chronic and acute inflammatory disorders, cancers, neurodegenerative disorders, traumatic brain injury and other diseases associated with mitochondrial disorders.

CypA is for example believed to play a critical role in the replication of the hepatitis C virus. Changes in expression of various Cyp isoforms have been associated with various cancers. CypA is overexpressed in human pancreatic cancer cells, non-small cell lung cancer and endometrial carcinoma. Both CypA and CypB are associated with breast cancer. CypA inhibitors have demonstrated clinical efficacy for treating hepatitis C infection and the mechanism of action suggests that similar efficacy would be observed for other viruses such as Dengue, West Nile or yellow fever viruses. Research has implicated extracellular CypA and CypB in the inflammation-mediated diseases such as asthma, severe sepsis, rheumatoid arthritis, COPD, age related macular degeneration among others. Broad spectrum Cyps inhibition may also protect the liver from fibrosis subsequent to non-alcoholic steatohepatitis, a common indication for liver transplantation after chronic hepatitis C.

CypD is an essential regulator of the opening of the mitochondrial permeability transition pore (MPTP) located in the mitochondrial matrix. The activation of the MPTP has been implicated in broad acute and traumatic events such as: spinal cord injury, traumatic brain injury, ischaemia/reperfusion injury, stroke, myocardial infarction, acute pancreatitis. The activation of the MPTP has also been implicated in chronic diseases such as congestive heart failure, Alzheimer's disease, Parkinson's disease, amyotrophic lateral sclerosis, multiple sclerosis, macular degeneration, epilepsy, diabetic retinopathy, liver disease and other diseases due to mitochondrial dysfunction.

NKTR is a cyclophilin-related protein receptor found in various cells types, including cells of the immune system, such as natural killer cells and a subset of T cells. In natural killer and T cells, NKTR mediates recognition of target cells for lysis. Recently, increased NKTR expression has been associated with progression of non-small cell lung carcinoma.

Due to the high similarity among the different isoforms, the design of different ligands that selectively bind to a specific subtype represents a major challenge in medicinal chemistry. It is widely thought that isoform-selective inhibitors are an advantage to enable targeting of Cyps for the treatment of various pathologies, such as viral infections, cancers and neurodegenerative diseases, but to date there are no demonstrated isoform selective small molecule Cyclophilin inhibitors or cyclophilin-like protein modulators.

The Cyps active site consists in two main subpockets, "Pro" and "Abu". Both pockets have been targeted by various Cyps binders reported so far in the literature. Beyond the two main pockets the cyclophilin's active site contains a more remote "3 o'clock" pocket, but it was previously reported that such pocket is too remote from the active site to be productively targeted (Structural and Biochemical Characterization of the Human Cyclophilin Family of Peptidyl-Prolyl Isomerases. Davis T L, Walker J R, Campagna-Slater V, Finerty P J, Paramanathan R, Bernstein G, MacKenzie F, Tempel W, Ouyang H, Lee W H, Eisenmesser E Z, Dhe-Paganon S. *PLoS Biology* 8(7): e1000439 2010).

Cyclosporin A (CsA) is a cyclic peptide comprising 11 amino acids that non-specifically inhibits Cyps. It is widely used for inhibition of CypA, however, the compound also inhibits CypB and CypD, and other Cyps. Furthermore, the use of CsA is limited due to its immunosuppressive properties, which is not a result of its binding to Cyps but from the interaction between the Cyp-CsA complex with calcineurin. Additionally, CsA only crosses the blood-brain barrier to a very limited extent, and has well documented side-effects such as kidney and liver dysfunction, pancreatitis, diarrhoea, convulsions, and ulcers which prevent its use in a number of Cyp-implicated conditions.

Alisporivir (DEB025), NIM811 and SCY-635 are analogues of CsA. By altering position four in the cyclic peptide the resulting complexes these compounds form with various Cyps are unable to bind calcineurin and are non-immunosuppressive. The isoform specificity does not differ to that of CsA. The development of DEB025 was put on hold after toxicity was observed when dosed in combination with ribavirin and pegylated interferon in anti-hepatitis C virus clinicial trials.

Sanglifehrins are not derived from CsA and are a group of naturally occurring Cyclophilin-binding polyketides. Non-immunosuppressive analogues of sanglifehrin A have been synthesized and two compounds (F680 and F684) showed significant inhibition of CypA, CypB, and CypD enzymatic activities. These two compounds are not isoform-specific inhibitors.

Examples of compounds providing inhibition of Cyclophilins are also disclosed in WO 2017/173048 and WO2011/076784.

There still remains the need to provide compounds providing inhibition of Cyclophilins with enhanced potency and/or advantageously featuring isoform selectivity over existing compounds. In particular, the burgeoning deployment of immunotherapy approaches for disease treatments, highlights the need for selectivity of action of cyclophilin ligands as more selective ligands could impact treatment outcome by reducing potential interference with immune cell action and/or directly modulating immune cell activity.

The present invention provides tri-vectors Cyps ligands, the first characterized example of small molecules that bind simultaneously to the Cyps active site (Abu and Pro pockets), and to a previously neglected 3 o'clock pocket. The binding mode of these novel compounds achieves enhanced potency and in some cases isoform selectivity.

STATEMENT OF THE INVENTION

The present invention provides a compound of formula (I),

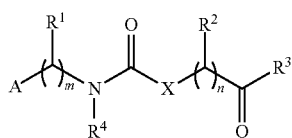

or a pharmaceutically acceptable salt thereof, wherein:

$R^1$ and $R^2$ are each independently is selected from the group consisting of —R, -haloalkyl, -hydroxyalkyl, —OR, —C(O)R, —CO2R, —C(O)N(R)2, —NRC(O)R, and —N(R)2; wherein $R^2$ could also be a sulphide;

each R is independently hydrogen, $C_{1-6}$ aliphatic, $C_{3-10}$ aryl, a 3-8 membered saturated or partially unsaturated carbocyclic ring, a 3-7 membered heterocylic ring having 1-4 heteroatoms independently selected from nitrogen, oxygen, sulphur, or a 5-6 membered monocyclic heteroaryl ring having 1-4 heteroatoms selected from nitrogen, oxygen, or sulphur;

$R^3$ is selected from the group consisting of —OEt, and

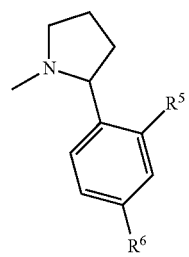

wherein $R^5$ and $R^6$ are independently selected from the group consisting of H, halide, methoxy, thiomethyl, morpholine and trifluoromethyl;

$R^4$ is selected from the group consisting of $C_{1-6}$-alkyl-, and $R^{4.1}$—$CH_2$— wherein, $R^{4.1}$ is $C_{3-6}$-cycloalkyl-, a 5-6 membered heterocyclic ring having 1-4 heteroatoms independently selected from nitrogen, oxygen, sulphur; optionally substituted with one $R^{4.1.1}$ wherein, $R^{4.1.1}$ is selected from —H, $C_{1-4}$-alkyl, optionally substituted with one substituent selected from $H_2N(O)C$— or $EtO(O)C$—;

X is carbon or nitrogen;

A is selected from the group consisting of 6 membered unsaturated ring, with 1-3 nitrogen atoms, which is optionally substituted by —$NH_2$, and

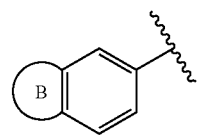

wherein ring B is a fused 5-10 membered saturated or partially unsaturated heterocyclic mono-bicyclic ring having 1-3 heteroatoms selected from nitrogen, oxygen or sulphur, which is optionally substituted by —OH; and m is 1 or 2; and n is 1 or 2.

The nitrogen atoms are within or attached to the 6 membered unsaturated ring.

Preferably the 6 membered unsaturated ring does not include any N atom within the ring and the 1-3 nitrogen atoms are present as substitutions on the ring.

According to one embodiment of the invention $R^3$ is —OEt.

According to another embodiment of the invention $R^3$ is

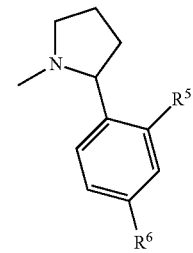

Then, preferably $R^6$ is H and $R^5$ is selected from the group consisting of —Br, —Cl, —OH, —OMe, —SMe, —$CF_3$, -morpholine and —H.

Preferably $R^4$ is selected from the group consisting of $C_{1-6}$-alkyl-, and $R^{4.1}$—$CH_2$— wherein, $R^{4.1}$ is -cyclopropyl, a 5-6 membered heterocyclic ring having 1-4 nitrogen atoms; optionally substituted with one $R^{4.1.1}$ wherein, $R^{4.1.1}$ is selected from —H, $C_{1-4}$-alkyl, optionally substituted with one substituent selected independently from $H_2N(O)C$— or $EtO(O)C$—;

According to one embodiment of the invention $R^1$ and $R^2$ in formula (I) are —H and X is nitrogen.

According to one embodiment of the invention A is selected from the group consisting of

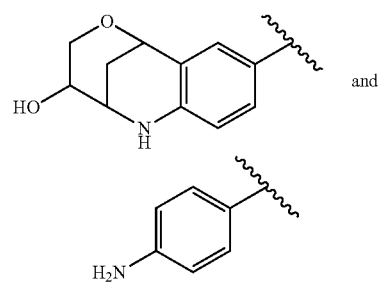

and

According to a further embodiment of the invention the compound has formula (II)

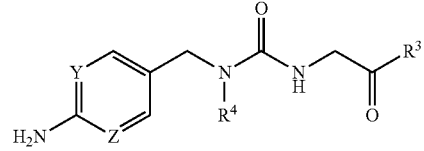
(II)

or a pharmaceutically salt thereof, wherein $R^3$ and $R^4$ are as defined above; Y is carbon or nitrogen and Z is carbon or nitrogen.

Then, preferably, Y and/or Z are carbon atoms.

According to one embodiment of the invention the compound is selected from the group consisting of 12
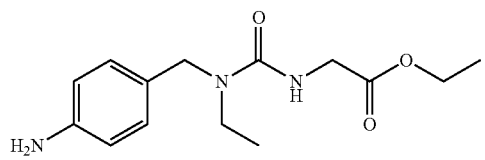

13
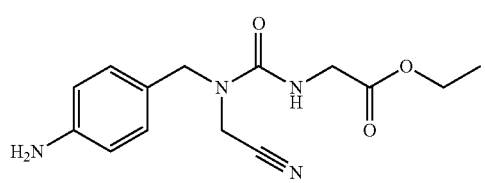

14
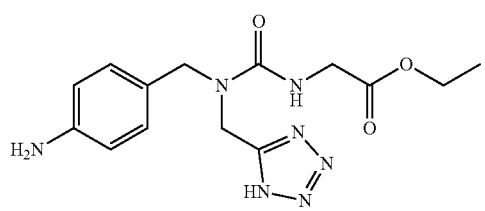

15
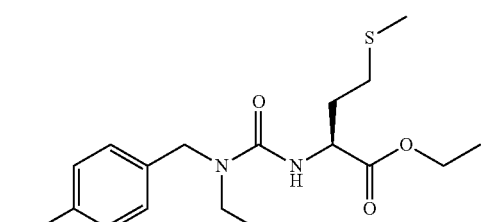

16
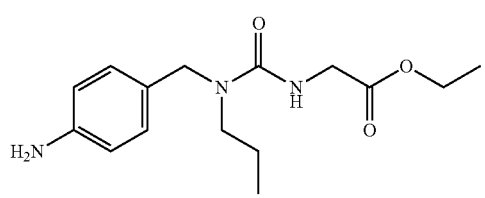

17
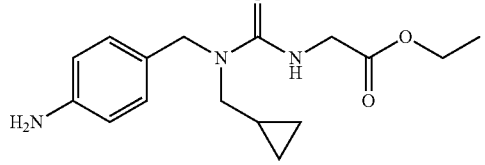

18
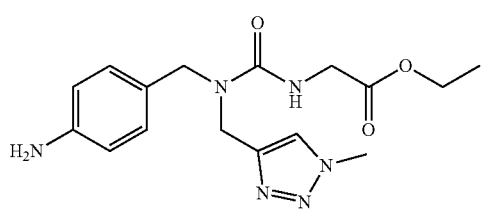

19
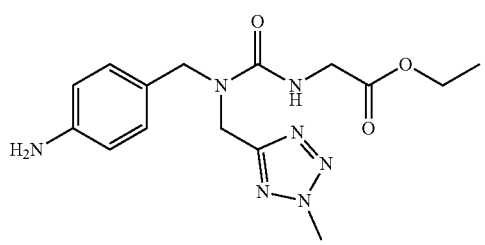

20
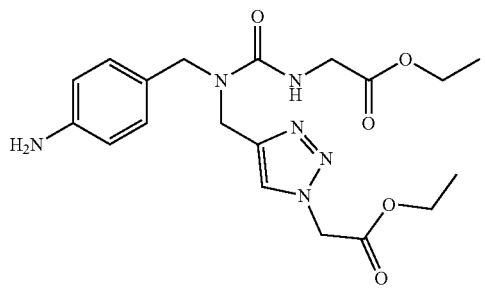

21
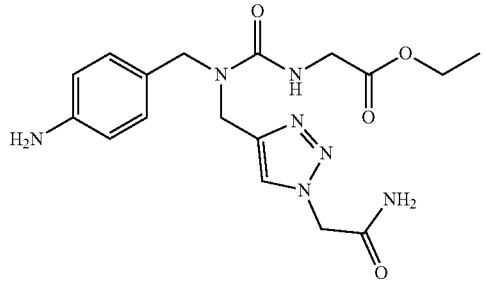

22
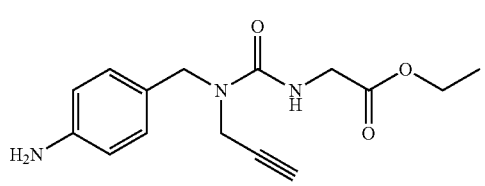

23 and a pharmaceutically acceptable salt thereof.

According to another embodiment of the invention the compound is selected from the group consisting of
9
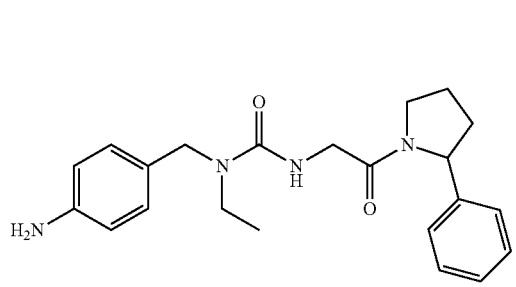
10
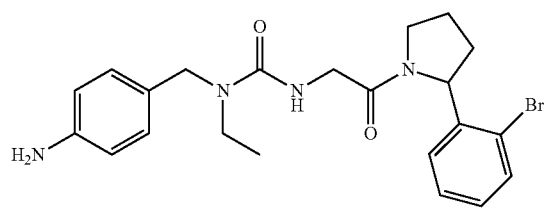
11
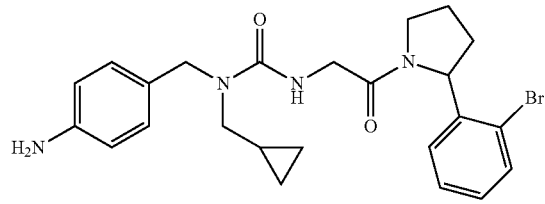
and a pharmaceutically acceptable salt thereof.
According to a further embodiment of the invention the compound is selected from the group consisting of
1
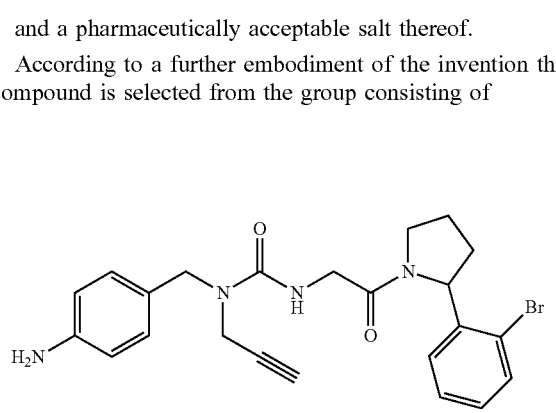
2
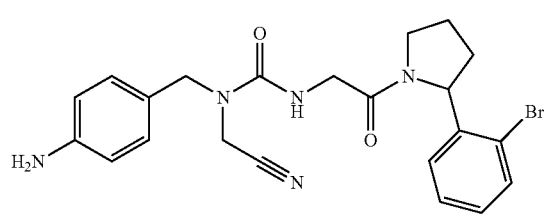
3
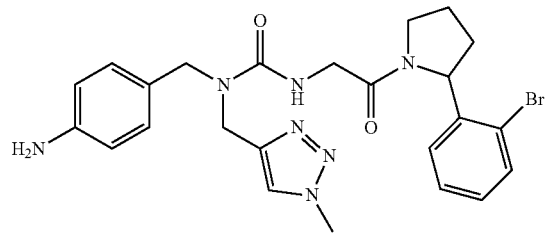
4
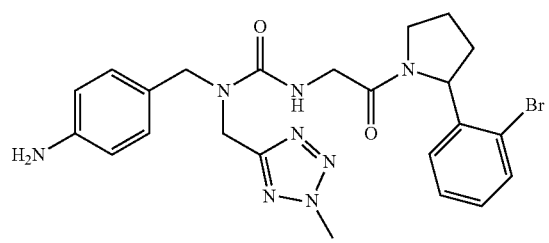
5
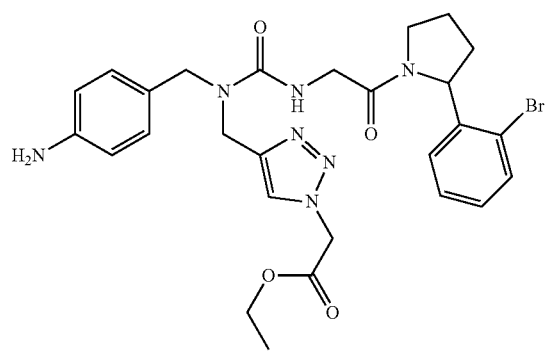
6
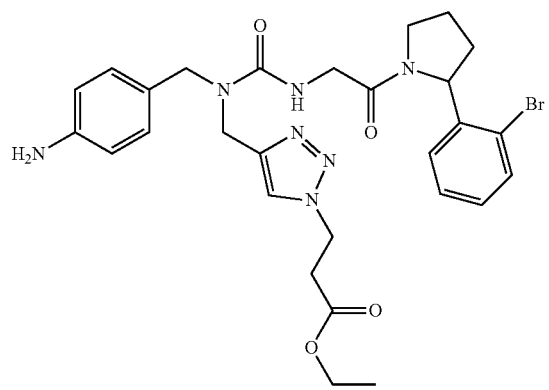
7
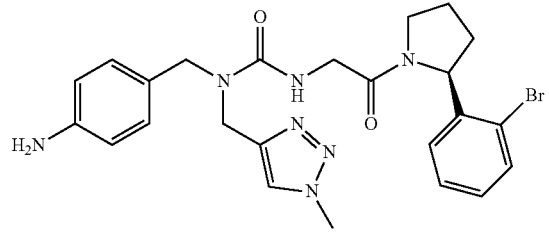

9

-continued

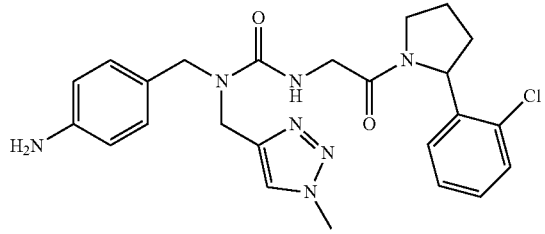

8 and a pharmaceutically acceptable salt thereof.

10

The present invention further provides a pharmaceutically acceptable composition comprising the compound and pharmaceutically acceptable salts thereof as described above. The composition may comprise a compound of the invention or a pharmaceutically acceptable salt thereof and a pharmaceutically acceptable carrier, adjuvant, or vehicle.

The amount of compound in the compositions of this invention is such that is effective to measurably inhibit cyclophilins in a biological sample or in a patient.

The present invention further provides a process for preparing the compounds of formula (I) comprising the steps of:

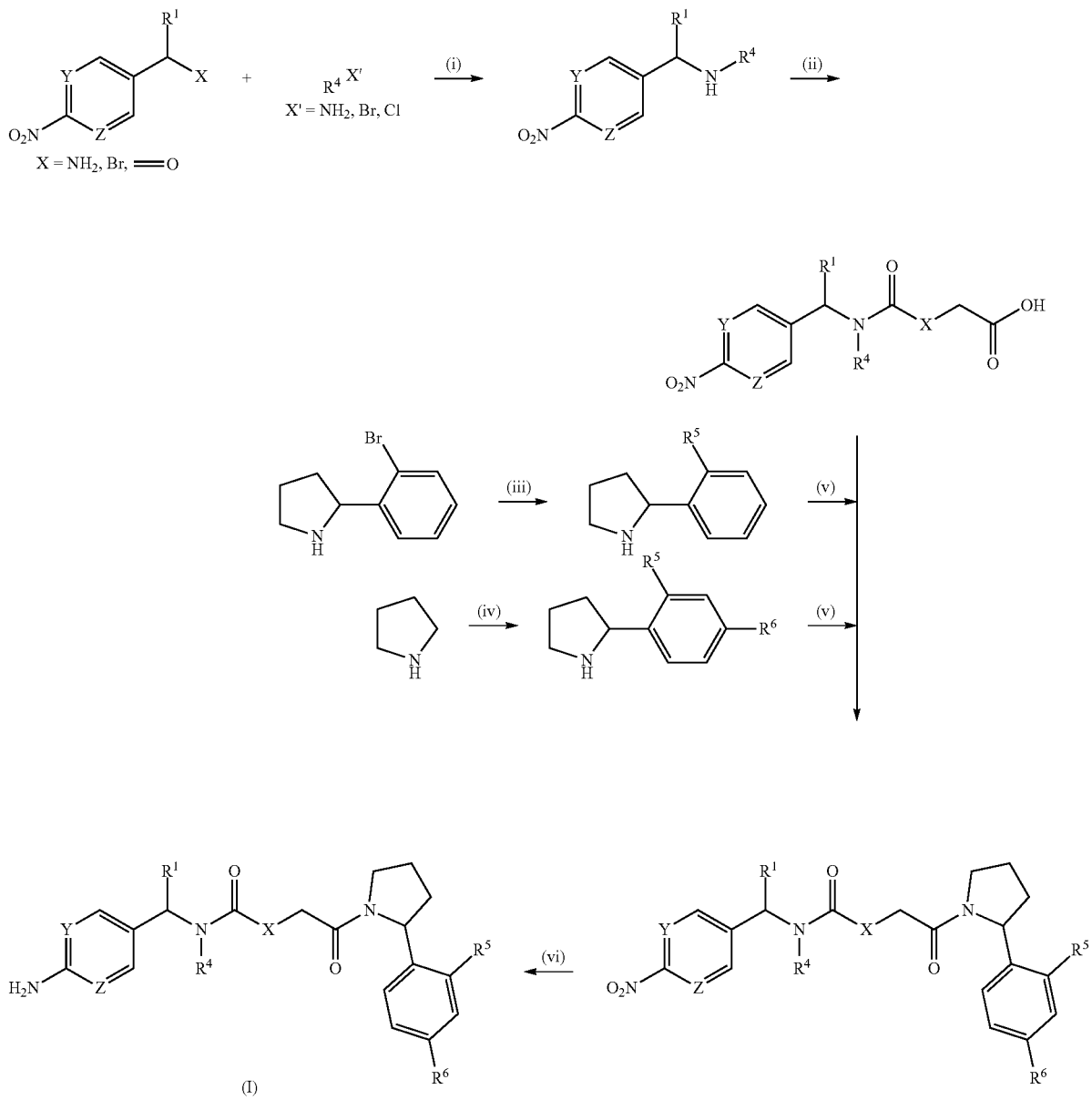

(i) Condensation or reductive amination
(ii) Urea or carbamate formation
(iii) Cross coupling
(iv) Deprotonative aryl coupling
(v) Amide coupling
(vi) Nitro reduction The present invention also provides the compound and/or a pharmaceutically acceptable salt thereof as described above for use in medicine, preferably in the treatment of a cyclophilin-mediated disease or disorder or for modulation of cyclophilin or cyclophilin-like protein induced signalling in cells wherein such signalling modulation is beneficial for the treatment of a disease or disorder.

The present invention also provides the pharmaceutically acceptable composition comprising the compound and/or a pharmaceutically acceptable salt thereof as described above for use in the treatment of a cyclophilin-mediated disease or disorder.

In certain embodiments, the invention further provides a method for inhibiting cyclophilins in a patient or in a biological sample comprising the step of administering to said patient or contacting said biological sample with a compound and/or a pharmaceutically acceptable salt thereof according to the invention.

The compounds are characterized by such a high affinity to cyclophilins, which ensures a reliable binding and preferably inhibition of cyclophilins. In certain embodiments, the substances are mono-specific in order to guarantee an exclusive and directed recognition with the single cyclophilins target.

In certain embodiments, the method for inhibiting cyclophilins is performed in-vitro.

In certain embodiments, the invention provides a method for preventing, treating or ameliorating in a subject a disease, disorder, or condition that is causally related to the aberrant activity of cyclophilins, which comprises administering to a subject a therapeutically effective amount of a compound of any formulae herein, or a pharmaceutically acceptable salt thereof.

In certain embodiments, the present invention provides a method for modulating or inhibiting cyclophilin activity in a patient comprising administering to the patient a compound of any formulae herein, or a pharmaceutically acceptable salt thereof, or composition of the present invention. In another embodiment, the present invention provides a method for modulating or inhibiting cyclophilin activity in a biological sample comprising administering a compound of any formulae herein, or a pharmaceutically acceptable salt thereof, or a composition of the present invention.

The disease or disorder may be selected from the group consisting of fibrosis of the kidney, liver, lung or pancreas, cardiac failure, viral infections, and inflammation.

In particular, the disease or disorder may be cancer, Alzheimer's disease, Parkinson's disease, Amyotrophic Lateral Sclerosis (ALS), Dementia, Multiple Sclerosis, Huntington's disease.

The disease or disorder may also be, pneumonia, bacteremia, trauma, tuberculosis, parasitic disease, neuroinflammation, schizophrenia, depression, neurodegenerative disease, and pain.

The disease or disorder may be selected from Human Immunodeficiency Virus (HIV), Hepatitis A-D, Human Papilloma Virus (HPV), and Herpes, including Herpes Simplex I and II, as well as the Epstein Barr Virus.

The disease or disorder may be a disease or disorder treatable using immunotherapy.

In certain embodiments, the invention provides for the treatment of diseases, disorders, and conditions characterized by excessive or abnormal cell proliferation. Such diseases include a proliferative or hyperproliferative disease. Examples of proliferative and hyperproliferative diseases include cancer and myeloproliferative disorders.

In another aspect, the invention provides for a kit consisting of separate packs of an effective amount of a compound according to the invention and/or pharmaceutically acceptable salts thereof, or a composition of the invention and optionally, an effective amount of a further active ingredient. The kit may comprise suitable containers, such as boxes, individual bottles, bags or ampoules. The kit may, for example, comprise separate ampoules, each containing an effective amount of a compound according to the invention and/or pharmaceutically acceptable salts or a composition of the invention, and an effective amount of a further active ingredient in dissolved or lyophilized form.

Compounds and/or pharmaceutically acceptable salts thereof, or compositions of the present invention may be administered orally, parenterally, by inhalation spray, topically, rectally, nasally, buccally, vaginally or via an implanted reservoir. Preferably, they are administered orally, intraperitoneally or intravenously. Most preferably, pharmaceutically acceptable compositions of this invention are formulated for oral administration. Exemplary oral dosage forms are capsules, tablets, aqueous suspensions or solutions. Such compositions are prepared according to techniques well-known in the art of pharmaceutical formulation.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like.

Compounds and/or pharmaceutically acceptable salts thereof, or compositions of the present invention may be administered to humans and other animals.

Definitions

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to "carbocyclic", "cycloaliphatic" or "cycloalkyl"), that has a single point of attachment to the rest of the molecule. Unless otherwise specified, aliphatic groups contain 1-6 aliphatic carbon atoms.

The term "lower alkyl" refers to a C1-4 straight or branched alkyl group. Exemplary lower alkyl groups are methyl, ethyl, propyl, isopropyl, butyl, isobutyl, and tert-butyl.

The term "lower haloalkyl" refers to a C straight or branched alkyl group that is substituted with one or more halogen atoms.

The term "heteroatom" means one or more of oxygen, sulfur, nitrogen, or phosphorus.

The term "unsaturated", as used herein, means that a moiety has one or more units of unsaturation.

The term "halogen" means F, Cl, Br, or I.

The term "aryl" used alone or as part of a larger moiety as in "aralkyl", "aralkoxy", or "aryloxyalkyl", refers to monocyclic and bicyclic ring systems having a total of five to fourteen ring members, wherein at least one ring in the system is aromatic and wherein each ring in the system contains three to seven ring members. The term "aryl" is used interchangeably with the term "aryl ring". In certain embodiments of the present invention, "aryl" refers to an aromatic ring system.

As used herein, the term "heterocyclic ring" refers to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. A heterocyclyl ring is optionally mono- or bicyclic.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, certain compounds of the invention contain "optionally substituted" moieties. In general, the term "substituted", whether preceded by the term "optionally" or not, means that one or more hydrogens of the designated moiety are replaced with a suitable substituent. "Substituted" applies to one or more hydrogens that are either explicit or implicit from the structure.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange.

Structures depicted herein are also meant to include all isomeric (e.g., enantiomeric, diastereomeric, tautomers, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention.

Additionally, structures depicted herein are also meant to include compounds that differ only in the presence of one or more isotopically enriched atoms. For example, compounds having the present structures including the replacement of hydrogen by deuterium or tritium, or the replacement of a carbon by a <13>C— or <14>C-enriched carbon are within the scope of this invention.

The term "patient" or "subject", as used herein, means an animal, preferably a mammal, and most preferably a human.

The term "pharmaceutically acceptable carrier, adjuvant, or vehicle" refers to a nontoxic carrier, adjuvant, or vehicle that does not destroy the pharmacological activity of the compound with which it is formulated.

The terms, "disease", "disorder", and "condition" may be used interchangeably here to refer to a cyclophilin mediated medical or pathological condition. The term "cyclophilin mediated condition", as used herein, means any disease state or other deleterious condition in which cyclophilins are known to play a role. The term "cyclophilin mediated condition" or "disease" also means those diseases or conditions that are alleviated by treatment with a cyclophilin inhibitor.

BRIEF DESCRIPTION OF THE FIGURE

FIG. 1 shows (A) a depiction of a type-I binding mode for prior-art compounds (B) a depiction of a type-II binding mode for novel tri-vector compounds disclosed in this invention. (C) co-crystal structure of CypA with a prior-art compound in a type-I binding mode. (D) co-crystal structure of CypA with tri-vector compound 12 that adopts a type-I binding mode. (E) co-crystal structure of CypA with tri-vector compound 19 that adopts a type-II binding mode. (F) co-crystal structure of CypA with tri-vector compound 4 that adopts a type-II binding mode.

EXAMPLES

Synthesis of Selected Compounds

Compounds have been prepared by the synthetic procedures shown in Scheme 1.

Scheme 1

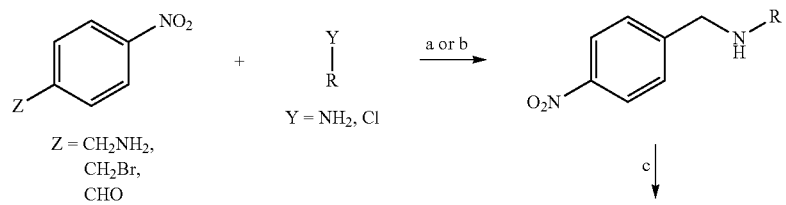

-continued

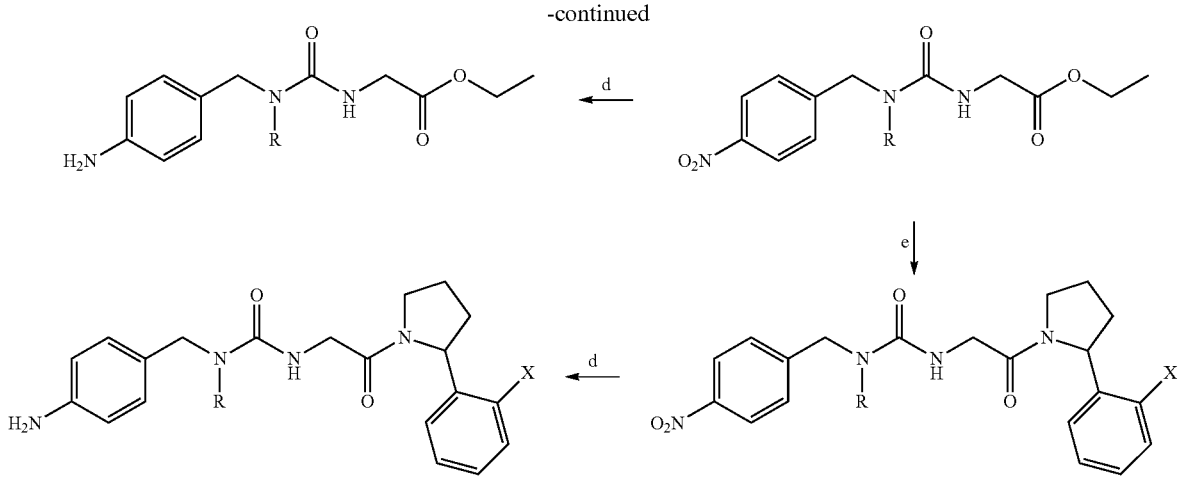

The first key intermediate of the synthesis, namely the substituted amino derivative, can be prepared from either p-nitrobenzaldehyde using a reductive amination procedure, or from a p-nitrophenyl derivative by a nucleophilic substitution reaction. The urea moiety is obtained by reaction with ethyl isocyanatoacetate. After hydrolysis of the ester, the corresponding carboxylic acid undergoes an amide coupling reaction with the haloarylpirrolidine derivative. Reduction of the nitro group led to the synthesis of the desired final products. Where intermediates were not commercially available, they were prepared according to reported procedures. Details concerning the preparations methods are provided below.

Chemicals, Materials, and Methods

Abbreviations used in the description of the examples that follow are: Acetonitrile (MeCN); ammonium chloride (NH$_4$Cl); BnBr (benzyl bromide); carbonyldiimidazole (CDI); cesium carbonate (Cs$_2$CO$_3$); cyclohexane (Cy); chloroform (CHCl$_3$); deuterated dimethylsulfoxyde (DMSO-d6); dichloromethane (DCM); dimethylsulfoxyde (DMSO); N,N-diisopropylethylamine (DIPEA); dimethylformamide (DMF); di-tert-butyldicarbonate (Boc$_2$O); 4-(dimethylamino)-pyridine (DMAP); ethylene glycol monomethyl ether (EGME); ethanol (EtOH); electrospray ionization (ESI); ethyl acetate (EtOAc); hydrochloric acid (HCl); mass spectrometry (MS); microwave (MW); sulfuric acid (H$_2$SO$_4$); iodomethane (MeI); N,N-dimethylformamide (DMF); lithium hydroxide (LiOH); magnesium sulphate (MgSO$_4$); methanol (MeOH); nuclear magnetic resonance (NMR); room temperature (RT); palladium acetate (Pd(OAc)$_2$); potassium carbonate (K$_2$CO$_3$); sodium bicarbonate (NaHCO$_3$); sodium borohydride (NaBH$_4$); tetrabutylammonium iodide (TBAI); triethylsilane (TES); tetrahydrofurane (THF); thin layer chromatography (TLC); triethylamine (Et$_3$N or TEA) and trifluoroacetic acid (TFA).

Automated column chromatography purifications were conducted using Biotage Isolera One apparatus with pre-packed silica gel columns of different sizes (10 and 25 g).

Mixtures of increasing polarity of cyclohexane and ethyl acetate or dichloromethane and methanol were used as eluents.

Microwave heating was performed using Biotage Initiator instrument.

Nuclear magnetic resonance (NMR) spectra were recorded at ambient temperature (298 K, unless otherwise stated) on a Bruker AVA400, AVA500 or AVA600 spectrometer running at 400, 500, or 601 MHz ($^1$H spectra) or 101, 126, 151 Hz ($^{13}$C spectra, respectively). Chemical shifts (δ values) are reported in parts-per-million (ppm) relative to tetramethylsilane ($^1$H and $^{13}$C spectra; δTMS=0) and are calibrated to the residual solvent peak.

Mass spectra were obtained by electrospray ionization (ESI) on a Bruker microTOF II mass spectrometer. Mass-to-charge ratios (m/z) of all parent (molecular) ions ([M]+/) and their intensities are reported, followed by (major) fragment or adduct ions and their intensities. LC-MS analyses were run on a Bruker microTOF II system equipped with an electrospray ionization interface and a photodiode array detector. PDA range was 210-400 nm.

Electrospray ionization was applied in positive modes.

UPLC mobile phases were (A) H$_2$O/Formic Acid (99.9:0.1), and (B) MeCN/Formic acid (99.9:0.1). Analyses were performed with the method reported below. Gradient: 5-100% B over 10 min. Flow rate: 200 µL/min. Temperature: 30° C. Column: Phenomenex Kinetex C18 (5 µm, 2.1 mm×50 mm). Melting points (mp) were determined on a Gallenkamp Electrothermal Melting Point apparatus.

General Procedure 1 for the Synthesis of the N-Substituted p-Nitrobenzylamine Derivatives (Steps a and b, Scheme 1)

Method A (Reductive Amination)

To a solution of p-nitrobenzaldehyde (1 eq.) in dry ethanol was added the amine derivatives (1.1 eq.) under a nitrogen atmosphere. The solution was stirred at room temperature for 16 hours and then refrigerated to 0° C., and NaBH$_4$ (2 eq.) was added portionwise until disappearance of the intermediate imine (TLC analysis, approximately 8 hours). The reaction mixture was concentrated in vacuo and the residue dissolved in DCM. The organic phase was washed sequentially with a saturated solution of NaHCO$_3$, water and brine, dried over MgSO$_4$, filtered, and concentrated in vacuo to yield the title compounds as pale-yellow oils, which were used without further purification.

Method B (Nucleophilic Substitution).

A mixture of 4-nitrobenzyl bromide or 4-nitrobenzylamine hydrochloride (1 eq.), alkyl amines or alkyl halides (1 eq.) and K$_2$CO$_3$ (2 eq.) in acetonitrile was stirred at 70° C. for 6 hours. The suspension was filtered and the residue washed with acetone several times. The filtrates were concentrated under reduced pressure to give the desired intermediates as oily products, which were pure enough for the next step.

General Procedure 2 for the Synthesis of Urea Derivatives (Step c, Scheme 1)

Ethyl isocyanatoacetate (1 eq.) was dissolved in DCM. p-nitrophenylamino intermediates (1 eq.) were added and the reaction mixture was stirred at room temperature overnight. After this time, water was added to the mixture and the organic phase was collected. The water phase was back-extracted with DCM several times and the combined organic phases were dried over MgSO$_4$, filtered, and evaporated under reduced pressure, yielding the products as an oil.

General Procedure 3 for the Synthesis of the Amide Derivative (Step e, Scheme 1)

Ethyl ester derivatives (1 eq.) were dissolved in a 1:1 mixture of THF/MeOH and treated with LiOH monohydrate (5 eq.) dissolved in water (Water/THF/MeOH ratio: 1:2:2). The reaction was kept under stirring at RT for 2 hours, then the reaction mixture was concentrated, diluted with water and washed with DCM. The aqueous phase was treated with 1 N aqueous HCl until acidic pH and extracted several times with EtOAc. The combined ethyl acetate organic phases were dried over MgSO$_4$, filtered, and evaporated to afford the desired products, which were used directly in the next step.

2-(2-Bromophenyl)-pyrrolidine (1 eq.), carboxylic acid derivatives (1.1 eq.) and HATU (1.4 eq.) were dissolved in DMF. DIPEA (1.5 eq.) was added and the reaction mixture was stirred at room temperature for 18 hours. After this time, the reaction mixture was diluted with EtOAc and washed with water and brine. The organic layer was dried over MgSO$_4$, filtered and concentrated in vacuo. The crude product was purified by flash column chromatography eluting with MeOH in DCM. The desired compounds were obtained as an oily product.

General Procedure 4 for the Synthesis of the Final Aniline Derivatives (Step d, Scheme 1)

p-nitrophenylurea intermediates (1 eq.) were placed in a round-bottomed flask and ethanol was added. Fe powder (3 eq.) was added and the reaction taken to reflux temperature (90° C.) at which time water (EtOH/water ratio: 10:2) was added through the top of the condenser together with calcium chloride (1 eq.). After 4 hours the reaction was allowed to cool and filtered through Celite. The reaction solvent was removed under reduced pressure by rotary evaporator, yielding a crude which was dissolved in DCM and washed with water and the organic phase was collected, dried over magnesium sulfate, filtered and concentrated, yielding the crude as a yellow oil. The resultant crude was purified by column chromatography on silica gel (DCM/MeOH 9:1). The organic fractions were collected and evaporated, yielding the desired compounds as an oily product.

Synthesis of the Intermediates

Ethyl[(4-nitrophenyl)methyl]amine

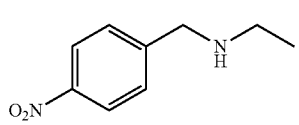

The title compound was synthesized applying the general procedure 1 method A using 4-nitrobenzaldehyde (500 mg, 3.31 mmol), dry ethanol (10 mL), ethylamine (2 M solution in THF, 1.80 mL, 3.64 mmol) and NaBH$_4$ (250 mg, 6.62 mmol). Yellow oil 555 mg (93%). LC-MS: Rt 2.8 min; m/z 181 [M+H]$^+$. $^1$H NMR (601 MHz, DMSO-d6) δ 8.19-8.16 (m, 2H), 7.63-7.59 (m, 2H), 3.81 (s, 2H), 2.51 (q, J=7.0 Hz, 2H), 2.21 (bs, 1H), 1.03 (t, J=7.1 Hz, 3H).

(Cyclopropylmethyl)[(4-nitrophenyl)methyl]amine

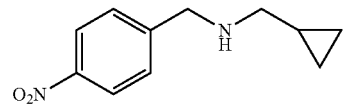 [SMILES: O=[N+]([O-])c1ccc(CNCC2CC2)cc1]

The title compound was synthesized applying the general procedure 1 method A using 4-nitrobenzaldehyde (620 mg, 4.10 mmol), dry ethanol (10 mL), cyclopropylmethylamine (0.40 mL, 4.51 mmol) and NaBH$_4$ (310 mg, 8.21 mmol). Yellow oil 800 mg (95%). LC-MS: Rt 2.9 min; m/z 207 [M+H]$^+$. $^1$H NMR (500 MHz, DMSO-d$_6$) δ 8.20-8.15 (m, 2H), 7.64-7.60 (m, 2H), 3.84 (s, 2H), 2.37 (d, J=6.7 Hz, 2H), 2.33 (s, 1H), 0.93-0.84 (m, 1H), 0.41-0.37 (m, 2H), 0.10-0.06 (m, 2H).

tert-butyl N-{[(1R,9S,10S)-10-hydroxy-12-oxa-8-azatricyclo[7.3.1.0$^{2,7}$]trideca-2,4,6-trien-4-yl]methyl}carbamate

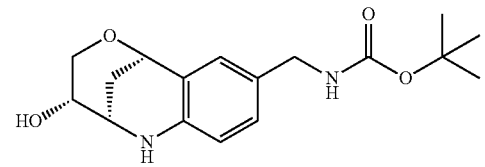 [SMILES: CC(C)(C)OC(=O)NCc1ccc2c(c1)[C@H]1C[C@@H](N2)[C@H](O)CO1]

A mixture of 2-deoxy-D-ribose (314 mg, 2.34 mmol), 4-[(N-Boc)aminomethyl]aniline (520 mg, 2.34 mmol) and Montmorillonite (1.2 g) were stirred at RT in MeCN (10 mL) for three days. The mixture was filtered through a celite pad and washed with methanol. The filtrate was concentrated under reduced pressure. The crude was purified by flash column chromatography on silica gel (hexane:EtOAc). 273 mg (36%). $^1$H NMR (500 MHz, DMSO-d$_6$) δ 6.82 (bs, 1H), 6.56 (d, J=8.2 Hz, 1H), 6.47 (d, J=8.2 Hz, 1H), 6.29 (s, 1H), 6.08 (s, 1H), 4.94 (d, J=3.9 Hz, 1H), 4.51 (s, 2H), 4.33 (t, J=5.1 Hz, 1H), 3.59 (dtd, J=10.8, 5.6, 3.1 Hz, 1H), 3.49-3.34 (m, 5H), 3.28 (bs, 1H), 1.39 (s, 9H)

(1R,9S,10S)-4-[(ethylamino)methyl]-12-oxa-8-azatricyclo[7.3.1.0$^{2,7}$]trideca-2,4,6-trien-10-ol

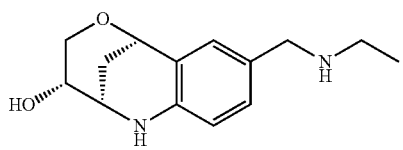 [SMILES: CCNCc1ccc2c(c1)[C@H]1C[C@@H](N2)[C@H](O)CO1]

To a solution of tert-butyl N-{[(1R,9S,10S)-10-hydroxy-12-oxa-8-azatricyclo[7.3.1.0$^{2,7}$]trideca-2,4,6-trien-4-yl]methyl}carbamate (520 mg, 1.62 mmol) in DCM was added 1 mL of 4N HCl in dioxane. The reaction was stirred for 1 h, then concentrated to give the intermediate which was used in the next step without purification. This crude material was dissolved in ethanol (10 mL) and acetaldehyde (0.1 mL, 1.9 mmol) added and stirred at room temperature for 12 h. NaBH$_4$ (144 mg, 3.8 mmol) was added and the reaction stirred for 6 h. The solvent was dissolved in water and the residue dissolved in water and acidified to pH 12 with 1 N NaOH. The mixture was extracted with ethyl acetate and concentrated to give the title compound as a yellow oil 199 mg (42%). This material was telescoped into the next reaction.

({[(4-nitrophenyl)methyl]amino}methyl)-1H-1,2,3-triazol-1-yl]acetate

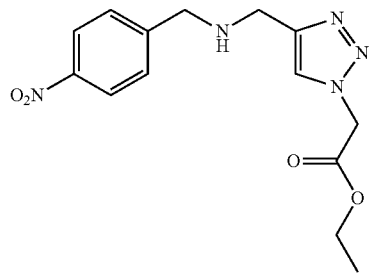 [SMILES: CCOC(=O)Cn1cc(CNCc2ccc([N+](=O)[O-])cc2)nn1]

To a solution of 2-{[(4-nitrophenyl)methyl]amino}acetonitrile (600 mg, 3.15 mmol), ethylazidoactetate (448 mg, 3.47 mmol) and CuSO$_4$ (201 mg, 1.26 mmol) was added sodium ascorbate (1.25 g, 6.31 mmol) and the mixture stirred at RT for 16 h. The reaction was quenched with crushed ice and extracted with ethyl acetate. The combined organic extracts were washed with brine, dried over anhydrous MgSO$_4$, filtered, and concentrated under reduced pressure to afford the desired compound. Brown oil 900 mg (89%). LC-MS: Rt 2.6 min; m/z 320 [M+H]$^+$. $^1$H NMR (601 MHz, DMSO-d$_6$) δ 8.23-8.17 (m, 2H), 8.00 (s, 1H), 7.69 (d, J=8.8 Hz, 1H), 7.64 (d, J=8.5 Hz, 1H), 5.41-5.34 (m, 2H), 4.22-4.11 (m, 4H), 4.11 (s, 1H), 3.74-3.69 (m 2H), 1.19 (t, J=7.1 Hz, 3H)

2-{[(4-nitrophenyl)methyl]amino}acetonitrile

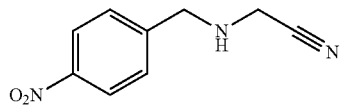 [SMILES: N#CCNCc1ccc([N+](=O)[O-])cc1]

The title compound was synthesized applying the general procedure 1 method B using 4-nitrobenzylamine hydrochloride (700 mg, 3.71 mmol), chloroacetonitrile (0.23 mL, 3.71 mmol) and K$_2$CO$_3$ (1026 mg, 7.42 mmol) in acetonitrile (10 mL). Brown oil 705 mg (99%). LC-MS: Rt 2.4 min; m/z 192 [M+H]$^+$. $^1$H NMR (500 MHz, DMSO-d$_6$) δ 8.24-8.15 (m, 2H), 7.66-7.58 (m, 2H), 3.90 (d, J=6.1 Hz, 2H), 3.65 (d, J=7.2 Hz, 2H), 3.29-3.23 (m, 1H).

[(4-nitrophenyl)methyl](prop-2-yn-1-yl)amine

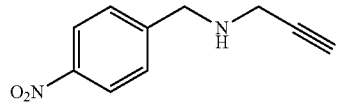

The title compound was synthesized applying the general procedure 1 method B using 4-nitrobenzyl bromide (700 mg, 3.24 mmol), propargylamine (0.21 mL, 3.24 mmol) and K$_2$CO$_3$ (896 mg, 6.48 mmol) in acetonitrile (10 mL). Brown oil 603 mg (98%). LC-MS: Rt 1.2 min; m/z 191 [M+H]$^+$. $^1$H NMR (601 MHz, DMSO-d$_6$) δ 8.20-8.17 (m, 2H), 7.64-7.59 (m, 2H), 3.88 (s, 2H), 3.81 (s, 1H), 3.31 (d, J=2.3 Hz, 2H), 3.11 (t, J=2.4 Hz, 1H).

[(4-nitrophenyl)methyl](propyl)amine

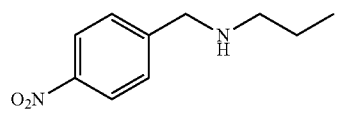

The title compound was synthesized applying the general procedure 1 method B using 4-nitrobenzyl bromide (700 mg, 3.24 mmol), 1-propylamine (0.27 mL, 3.24 mmol) and K$_2$CO$_3$ (896 mg, 6.48 mmol) in acetonitrile (10 mL). Brown oil 600 mg (95%). LC-MS: Rt 1.2 min; m/z 195 [M+H]$^+$. $^1$H NMR (500 MHz, DMSO-d$_6$) δ 8.20-8.14 (m, 2H), 7.64-7.58 (m, 2H), 3.80 (s, 2H), 2.44 (t, J=7.4 Hz, 2H), 2.23 (s, 1H), 1.43 (sxt, J=7.4 Hz, 2H), 0.87 (t, J=7.4 Hz, 3H).

(carbamoylmethyl)(diazyn-1-ium-1-yl)azanide

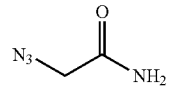

2-bromoacetamide (600 mg, 4.35 mmol) was dissolved in 10 mL of DMSO. Sodium azide (622 mg, 9.57 mmol) was added and the mixture stirred overnight at rt. The reaction was diluted with water and extracted with ethyl acetate. The combined organic phases were dried over anhydrous MgSO$_4$, filtered, and the solvent removed under reduced pressure to give the title compound as a colorless oil 650 mg (90%).

$^1$H NMR (601 MHz, DMSO-d$_6$) δ 7.52 (s, 1H), 7.25 (s, 1H), 3.78 (s, 2H).

21

2-[4-({[(4-nitrophenyl)methyl]amino}methyl)-1H-1,2,3-triazol-1-yl]acetamide

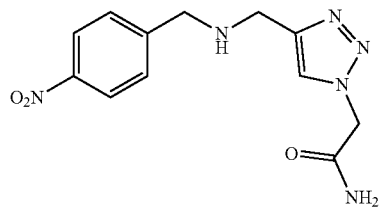 [SMILES: NC(=O)Cn1cc(CNCc2ccc([N+](=O)[O-])cc2)nn1]

A mixture of (carbamoylmethyl)(diazyn-1-ium-1-yl)azanide (347 mg, 3.47 mmol), [(4-nitrophenyl)methyl](prop-2-yn-1-yl)amine (600 mg, 3.15 mmol), CuSO$_4$ (503 mg, 3.15 mmol) and sodium ascorbate (1249 mg, 6.31 mmol) were dissolved in EtOH/water (20 mL, 1:1) and stirred at rt for 16 h. The reaction mixture was quenched with crushed ice and extracted with ethyl acetate. The combined organic fractions were washed with brine and dried over anhydrous MgSO$_4$, filtered and the solvent removed in vacuo. The crude oil was purified by column chromatography on silica gel (DCM/MeOH). Pale yellow solid 250 mg (27%). LC-MS: Rt 1.0 min; m/z 291 [M-Na]$^+$. $^1$H NMR (601 MHz, DMSO-d$_6$) δ 8.20 (d, J=8.3 Hz, 2H), 7.92 (s, 1H), 7.69 (s, 1H), 7.64 (d, J=8.3 Hz, 2H), 7.36 (s, 1H), 5.04 (s, 2H), 3.97-3.68 (d, J=66.3 Hz, 4H).

Ethyl 2[({[1-(carbamoylmethyl)-1H-1,2,3-triazol-4-yl]methyl}[(4-nitrophenyl)methyl]carbamoyl)amino]acetate

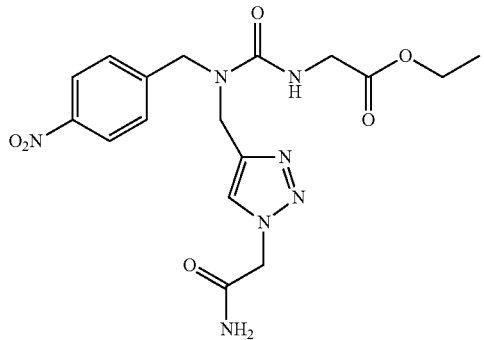 [SMILES: CCOC(=O)CNC(=O)N(Cc1ccc([N+](=O)[O-])cc1)Cc1cn(CC(N)=O)nn1]

The title compound was synthesized applying the general procedure 2 using 2-[4-({[(4-nitrophenyl)methyl]amino}methyl)-1H-1,2,3-triazol-1-yl]acetamide (250 mg, 0.86 mmol), Ethyl isocyanatoacetate (0.1 mL, 0.86 mmol) in 10 mL of DMF. Yellow oil 800 mg (97%). LC-MS: Rt 5.2 min; m/z 420 [M+H]$^+$. $^1$H NMR (500 MHz, DMSO-d$_6$) δ 8.19 (d, J=8.8 Hz, 2H), 7.93 (s, 1H), 7.70 (s, 1H), 7.48 (d, J=8.8 Hz, 2H), 7.38 (s, 2H), 5.05 (s, 2H), 4.61 (s, 2H), 4.48 (s, 2H), 4.09 (q, J=7.1 Hz, 2H), 3.79 (d, J=5.9 Hz, 2H), 1.19 (t, J=7.1 Hz, 3H). $^{13}$C NMR (126 MHz, DMSO-d$_6$) δ 171.45, 171.38, 167.68, 158.22, 157.94, 144.35, 128.99 (20), 125.29, 123.58 (20), 61.93, 60.65, 50.82, 48.76, 42.96, 14.45.

22 tert-butyl N-{2-[2-(2-chlorophenyl)pyrrolidin-1-yl]-2-oxoethyl}carbamate

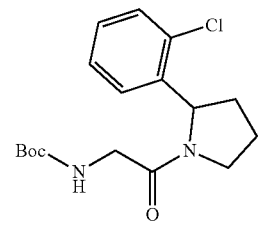 [SMILES: CC(C)(C)OC(=O)NCC(=O)N1CCCC1c1ccccc1Cl]

Pivaloyl chloride (0.2 mL, 1.54 mmol) was added to a solution of Boc-glycine (270 mg, 1.54 mmol) and Et$_3$N (0.5 mL, 3.47 mmol) in DCM (5 ml) at 0° C. The reaction was stirred for 1 h, where after Et$_3$N (0.5 mL, 3.47 mmol) and 2-(2-Chlorophenyl)-pyrrolidine (308 mg, 1.70 mmol) were added in succession. The reaction was allowed to warm to room temperature and react overnight. The reaction mixture was washed with aqueous 0.5 M citric acid, sat. NaCl and sat. NaHCO$_3$. The DCM phase was dried with anhydrous MgSO$_4$ and evaporated. 500 mg, 96%. $^1$H NMR (400 MHz, DMSO-d$_6$) δ 7.42 (td, J=6.0, 5.5, 2.9 Hz, 2H), 7.31-7.19 (m, 2H), 7.19-7.10 (m, 1H), 6.77 (t, J=5.8 Hz, 1H), 3.83 (qt, J=12.3, 5.9 Hz, 2H), 3.75-3.49 (m, 2H), 2.31-2.19 (m, 1H), 2.01-1.63 (m, 4H), 1.21 (s, 9H).

3-{2-[2-(2-chlorophenyl)pyrrolidin-1-yl]-2-oxoethyl}-1-[(4-nitrophenyl)methyl]-1-(prop-2-yn-1-yl)urea

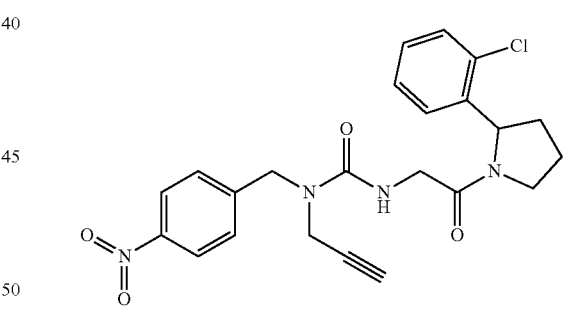

tert-butyl N-{2-[2-(2-chlorophenyl)pyrrolidin-1-yl]-2-oxoethyl}carbamate (460 mg, 1.36 mmol) was placed in a round-bottom flask followed by dry DCM (10 mL). 2-Chloropyridine (0.39 mL, 4.07 mmol) was added, followed by trifluoromethanesulfonic anhydride (0.34 mL, 2.04 mmol), and the reaction mixture was stirred for 50 min at room temperature. Then Et$_3$N (0.4 mL, 2.85 mmol) and 2-{[(4-nitrophenyl)methyl]amino}acetonitrile (516 mg, 2.72 mmol) were added, and the reaction mixture was stirred at room temperature for 20 h. The crude product was purified using column chromatography (30%-50% EtOAc in hexane) to afford the desired product of adequate purity for the next step.

3-{2-[2-(2-chlorophenyl)pyrrolidin-1-yl]-2-oxo-ethyl}-1-[(1-methyl-1H-1,2,3-triazol-4-yl)methyl]-1-[(4-nitrophenyl)methyl]urea

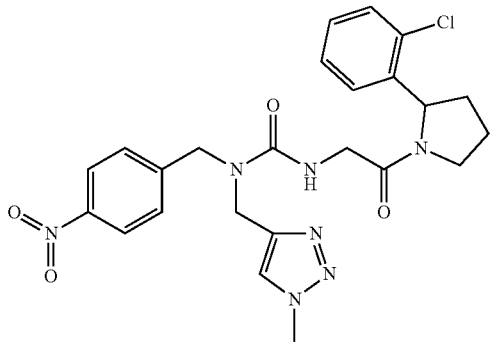 [SMILES: Cn1cc(CN(Cc2ccc([N+](=O)[O-])cc2)C(=O)NCC(=O)N2CCCC2c2ccccc2Cl)nn1]

To a solution of Iodomethane (0.1 mL, 1.6 mmol) in H$_2$O/DMF 1:4 (10 mL), NaN$_3$ (99 mg, 1.5 mmol), Na$_2$CO$_3$ (440 mg, 4.1 mmol), ascorbic acid (157 mg, 0.9 mmol), CuSO$_4$*5H$_2$O (148 mg, 0.6 mmol) and 3-{2-[2-(2-chlorophenyl)pyrrolidin-1-yl]-2-oxoethyl}-1-[(4-nitrophenyl)methyl]-1-(prop-2-yn-1-yl)urea (450 mg, 1.0 mmol) were added. The reaction mixture was stirred at rt overnight, diluted with saturated NH$_4$Cl, treated with solid EDTA and extracted with EtOAc. The combined organic extracts were washed with H$_2$O, dried over anhydrous MgSO$_4$, and concentrated under reduced pressure. The resulting residue was further purified by column chromatography on silica gel (Eluent: Chloroform/MeOH), as orange oil (196 mg, 39% yield). LC-MS: Rt 5.9 min; m/z 512 [M+H]$^+$. $^1$H NMR (500 MHz, DMSO-d$_6$) δ 8.16 (d, J=8.7 Hz, 2H), 7.96 (d, J=3.4 Hz, 1H), 7.63-7.45 (m, 2H), 7.46-7.41 (m, 1H), 7.40-7.30 (m, 1H), 7.30-7.12 (m, 2H), 6.77 (dt, J=39.7, 5.4 Hz, 1H), 5.41-5.22 (m, 1H), 4.58 (s, 1H), 4.06-3.98 (m, 2H), 3.92-3.84 (m, 1H), 3.68-3.58 (m, 2H), 2.90 (s, 3H), 2.35-2.21 (m, 1H), 2.00-1.66 (m, 3H).

tert-butyl N-[(4R)-4-(2-bromophenyl)-4-(methanesulfonyloxy)butyl]carbamate

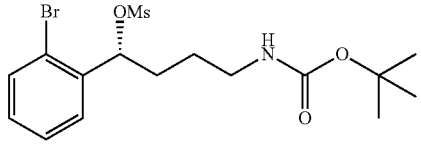 [SMILES: CC(C)(C)OC(=O)NCCC[C@@H](OS(C)(=O)=O)c1ccccc1Br]

Bromoiodobenzene (0.5 mL, 3.88 mmol) was added to iPrMgCl·LiCl (3 mL, 3.89 mmol) cooled to −15° C. and stirred for 30 minutes. Tert-butyl-2-oxopyrrolidine-1-carboxylate (0.68 mL, 3.97 mmol), was added and the reaction stirred at 0° C. for 2 h then left overnight at room temperature. NH$_4$Cl (sat, 20 mL) was added and the mixture extracted with ethyl acetate. The combined organic layers were dried over MgSO$_4$, filtered, and the solvent removed in vacuo. This crude was dissolved in THF (12 mL) and added dropwise to (R)-2-methyl-CBS-oxaborolidine (206 mg, 0.75 mmol) in BH$_3$-DMS (2.48 mL, 2.48 mmol). The reaction was stirred for 3 h at RT, quenched with 1M HCl, and extracted with ethyl acetate. The combined organic layers were dried over MgSO$_4$, filtered, and the solvent removed in vacuo to an oil (781 mg, 91%). The oil was dissolved in DCM (9 mL) and MsCl (0.51 mL, 6.57 mmol) and NEt$_3$ (1.22 mL, 8.76 mmol) added. The mixture was stirred at RT overnight. The mixture was washed with NaHCO$_3$, water and brine and dried over MgSO$_4$, filtered and the solvent removed in vacuo affording an oil which was used directly in the next step.

(2S)-2-(2-bromophenyl)pyrrolidine

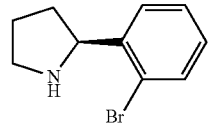 [SMILES: Brc1ccccc1[C@@H]1CCCN1]

tert-butyl N-[(4R)-4-(2-bromophenyl)-4-(methanesulfonyloxy)butyl]carbamate (739 mg, 1.75 mmol), was dissolved in DCM/TFA (12 mL, 5:1) and stirred at RT for 2 h. The mixture was concentrated in vacuo and the residue dissolved in 1 M NaOH (7 mL) in MeOH (6 mL) and stirred for 2 days at RT. The reaction was concentrated, neutralized with 1M HCl and extracted with ethyl acetate. The combined organic layers were dried over MgSO$_4$, filtered, and the solvent removed in vacuo. Yellow solid (395 mg, quant.) $^1$H NMR (601 MHz, DMSO-d$_6$) δ 7.70-7.65 (m, 1H), 7.57 (ddd, J=7.8, 5.4, 1.5 Hz, 1H), 7.50-7.42 (m, 1H), 7.42-7.33 (m, 1H), 3.94 (tt, J=7.4, 2.1 Hz, 1H), 3.32 (bs, 1H), 3.28-3.10 (m, 1H), 2.96-2.87 (m, 1H), 2.40-2.31 (m, 2H), 2.03-1.90 (m, 1H), 1.88-1.71 (m, 1H).

Ethyl 2-({ethyl[(4-nitrophenyl)methyl]carbamoyl}amino)acetate

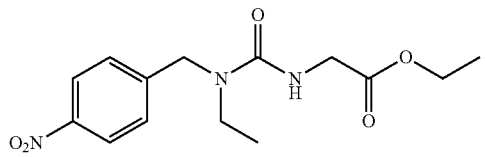 [SMILES: CCOC(=O)CNC(=O)N(CC)Cc1ccc([N+](=O)[O-])cc1]

The title compound was synthesized applying the general procedure 2 using Ethyl[(4-nitrophenyl)methyl]amine (480 mg, 2.66 mmol), Ethyl isocyanatoacetate (0.3 mL, 2.66 mmol) in 10 mL of DCM. Yellow oil 800 mg (97%). LC-MS: Rt 5.6 min; m/z 332 [M-Na]$^+$. $^1$H NMR (500 MHz, DMSO-d$_6$) δ 8.17-8.23 (m, 2H), 7.53-7.48 (m, 2H), 6.95 (t, J=5.9 Hz, 1H), 4.57 (s, 2H), 4.10 (q, J=6.9 Hz, 2H), 3.77 (d, J=6.0 Hz, 2H), 3.24 (q, J=7.0 Hz, 2H), 1.20 (t, J=7.1 Hz, 3H), 1.04 (t, J=7.0 Hz, 3H). $^{13}$C NMR (126 MHz, DMSO-d$_6$) δ 171.48, 157.88, 148.24, 146.95, 128.62 (2C), 123.90 (2C), 60.60, 48.95, 42.86, 41.49, 14.59, 13.81.

Ethyl 2-{[(cyclopropylmethyl)][(4-nitrophenyl)methyl]carbamoyl]amino}acetate

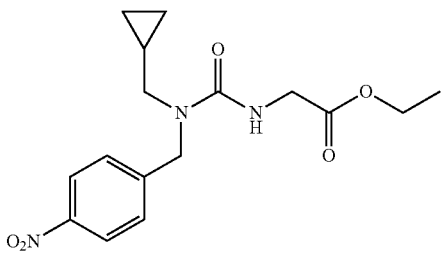 [SMILES: CCOC(=O)CNC(=O)N(Cc1ccc([N+](=O)[O-])cc1)CC1CC1]

The title compound was synthesized applying the general procedure 2 using (Cyclopropylmethyl)[(4-nitrophenyl)methyl]amine (380 mg, 1.84 mmol) and Ethyl isocyanatoacetate (0.2 mL, 1.84 mmol) in 10 mL of DCM. Yellow oil 500 mg (81%). LC-MS: Rt 5.8 min; m/z 358 [M-Na]⁺. ¹H NMR (500 MHz, DMSO-$d_6$) δ 8.23-8.13 (m, 2H), 7.54-7.46 (m, 2H), 6.98 (t, J=5.8 Hz, 1H), 4.67 (s, 2H), 4.14-4.07 (m, 2H), 3.76 (d, J=5.9 Hz, 2H), 3.13 (d, J=6.8 Hz, 2H), 1.24-1.14 (m, 3H), 0.95 (ddtd, J=11.7, 8.0, 6.8, 4.9 Hz, 1H), 0.40-0.31 (m, 2H), 0.21-0.12 (m, 2H). ¹³C NMR (126 MHz, DMSO-$d_6$) δ 171.45, 158.05, 148.24, 146.86, 128.47 (2C), 123.80 (2C), 60.88, 51.05, 49.59, 42.78, 14.58, 10.66, 3.81 (2C).

Ethyl 2-{[(cyanomethyl)][(4-nitrophenyl)methyl]carbamoyl]amino}acetate

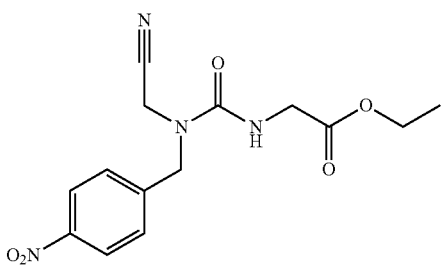 [SMILES: CCOC(=O)CNC(=O)N(CC#N)Cc1ccc([N+](=O)[O-])cc1]

The title compound was synthesized applying the general procedure 2 using 2-{[(4-nitrophenyl)methyl]amino}acetonitrile (600 mg, 3.14 mmol) and Ethyl isocyanatoacetate (0.35 mL, 3.14 mmol) in 10 mL of DCM. Brown oil 900 mg (90%). LC-MS: Rt 5.5 min; m/z 321 [M+H]⁺. ¹H NMR (500 MHz, DMSO-$d_6$) δ 8.26-8.21 (m, 2H), 7.58-7.54 (m, 2H), 7.51-7.48 (m, 1H), 4.72 (s, 2H), 4.38 (s, 2H), 4.13-4.09 (m, 2H), 3.83-3.79 (m, 2H), 1.22-1.19 (m, 3H). ¹³C NMR (126 MHz, DMSO-$d_6$) δ 170.95, 157.32, 147.30, 145.77, 128.84 (2C), 123.99 (2C), 67.48, 60.79, 50.49, 36.21, 25.60, 14.57.

Ethyl 2-({ethyl[(4-nitrophenyl)methyl]carbamoyl}amino)acetate

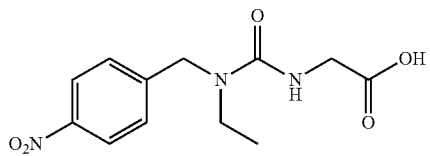 [SMILES: CCN(Cc1ccc([N+](=O)[O-])cc1)C(=O)NCC(=O)O]

The title compound was synthesized applying the general procedure 3 part 1 using Ethyl 2-({ethyl[(4-nitrophenyl)methyl]carbamoyl}amino)acetate (340 mg, 1.1 mmol) and LiOH (185 mg, 4.4 mmol) in THF/methanol (12 mL, 1:1). Yellow solid 230 mg (74%). ¹H NMR (500 MHz, DMSO-$d_6$) δ 12.38 (s, 1H), 8.20 (s, 2H), 7.51 (d, J=8.7 Hz, 2H), 6.84 (t, J=5.9 Hz, 1H), 4.56 (d, J=6.1 Hz, 2H), 3.71 (t, J=6.2 Hz, 2H), 3.23 (q, J=7.1 Hz, 2H), 1.03 (t, J=7.0 Hz, 3H). ¹³C NMR (126 MHz, DMSO-$d_6$) δ 172.96, 157.96, 148.34, 146.94, 128.69 (2C), 123.89 (2C), 60.22, 48.96, 21.23, 13.84.

3-{2-[2-(2-bromophenyl)pyrrolidin-1-yl]-2-oxoethyl}-1-ethyl-1-[(4-nitrophenyl)methyl]urea

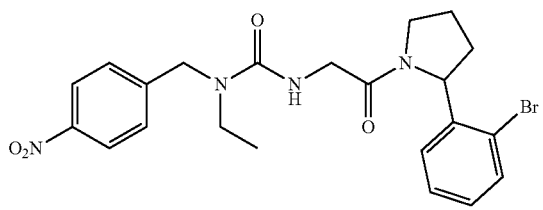 [SMILES: CCN(Cc1ccc([N+](=O)[O-])cc1)C(=O)NCC(=O)N1CCCC1c1ccccc1Br]

The title compound was synthesized applying the general procedure 3 part 1 using Ethyl 2-({ethyl[(4-nitrophenyl)methyl]carbamoyl}amino)acetate (224 mg, 0.8 mmol), 2-(2-bromo)-pyrrolidine (150 mg, 0.66 mmol), HATU (328 mg, 0.86 mmol) and DIPEA (0.2 mL, 1.00 mmol), in DMF (15 mL). The product was purified by column chromatography (EtOAc/hexane) colourless liquid 100 mg (31%). LC-MS: Rt 6.2 min; m/z 491 [M+H]⁺. ¹H NMR (500 MHz, DMSO-$d_6$) δ ¹H NMR (500 MHz, Chloroform-d) δ 8.14 (dd, J=8.8, 1.9 Hz, 2H), 7.55 (ddd, J=14.6, 7.9, 1.3 Hz, 1H), 7.42-7.37 (m, 2H), 7.30-7.19 (m, 1H), 7.12 (dtd, J=28.5, 7.7, 1.7 Hz, 1H), 6.99 (ddd, J=39.6, 7.7, 1.7 Hz, 1H), 5.48-5.41 (m, 1H), 4.59 (q, J=16.5 Hz, 1H), 4.55 (s, 1H), 4.15 (d, J=4.0 Hz, 1H), 4.11 (q, J=7.1 Hz, 1H), 3.89-3.69 (m, 1H), 3.62 (ddd, J=10.0, 8.7, 7.2 Hz, 1H), 3.35 (dd, J=17.5, 3.5 Hz, 1H), 3.31-3.19 (m, 2H), 2.44 (dddd, J=12.7, 11.2, 8.0, 6.9 Hz, 1H), 2.34 (dddd, J=12.6, 10.4, 8.2, 7.0 Hz, 1H), 2.02-1.95 (m, 1H), 1.95-1.87 (m, 1H), 1.25 (t, J=7.1 Hz, 1H), 1.19-1.09 (m, 2H).

3-{2-[2-(2-bromophenyl)pyrrolidin-1-yl]-2-oxoethyl}-1-(cyclopropylmethyl)-1-[(4-nitrophenyl)methyl]urea

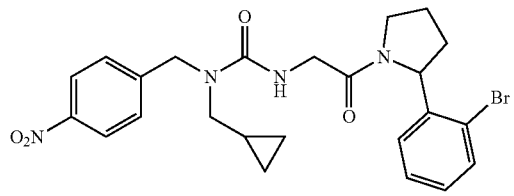 [SMILES: O=C(NCC(=O)N1CCCC1c1ccccc1Br)N(Cc1ccc([N+](=O)[O-])cc1)CC1CC1]

The title compound was synthesized applying the general procedure 3 Ethyl 2-{[(cyclopropylmethyl)][(4-nitrophenyl)methyl]carbamoyl]amino}acetate (350 mg, 1.04 mmol) and LiOH (219 mg, 5.22 mmol), in THF/water (8 mL, 1:1) followed by HATU (235 mg, 0.62 mmol), and 2-(2-bromophenyl)-pyrrolidine (100 mg, 0.44 mmol) and DIPEA (0.12 mL, 0.66 mmol). The crude product was purified by flash column chromatography eluting DCM/MeOH to yield the product as a brown oil 110 mg, (48%). ¹H NMR (600 MHz, Chloroform-d) δ 7.95 (apt, J=8.8 Hz, 2H), 7.38 (dddd, J=49.7, 23.1, 7.9, 1.5 Hz, 1H), 7.26 (d, J=8.7 Hz, 2H), 7.18-6.96 (m, 1H), 6.95-6.76 (m, 1H), 4.54 (q, J=7.1 Hz, 2H), 4.02-3.97 (m, H), 3.96-3.89 (m, 2H), 3.71-3.63 (m, 2H), 3.60-3.43 (m, 2H), 3.06-2.92 (m, 2H), 2.36-2.11 (m, 1H), 1.86-1.57 (m, 2H), 1.08 (t, J=7.1 Hz, 3H), 0.86-0.71 (m, 2H), 0.30 (ddd, J=20.5, 8.1, 1.2 Hz, 1H).

3-{2-[(2S)-2-(2-bromophenyl)pyrrolidin-1-yl]-2-oxoethyl}-1-[(1-methyl-1H-1,2,3-triazol-4-yl)methyl]-1-[(4-nitrophenyl)methyl]urea

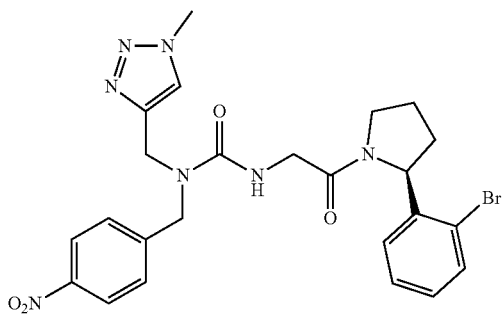 [SMILES: Cn1cc(CN(Cc2ccc([N+](=O)[O-])cc2)C(=O)NCC(=O)N2CCC[C@H]2c2ccccc2Br)nn1]

The title compound was synthesised according to the general procedure 3 using Ethyl 2-({[(1-methyl-1H-1,2,3-triazol-4-yl)methyl][(4-nitrophenyl)methyl]carbamoyl}amino)acetate (752 mg, 2.00 mmol), LiOH (419 mg, 9.99 mmol) in THF/MeOH (8 mL, 1:1). The acid was then coupled with (2S)-2-(2-bromophenyl)pyrrolidine (150 mg, 0.66 mmol), using HATU (353 mg, 0.93 mmol) and DIPEA (0.17 mL, 1.0 mmol). Brown oil (111 mg, 30%). LC-MS: Rt 1.1 min; m/z 556 [M+H]⁺.

2-{[(cyanomethyl)[(4-nitrophenyl)methyl]carbamoyl]amino}acetic acid

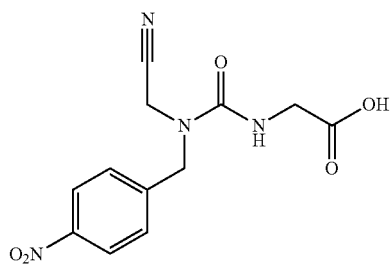 [SMILES: N#CCN(Cc1ccc([N+](=O)[O-])cc1)C(=O)NCC(=O)O]

The title compound was synthesized applying the general procedure 3 using Ethyl 2-{[(cyanomethyl)[(4-nitrophenyl)methyl]carbamoyl]amino}acetate (450 mg, 1.4 mmol) and LiOH (295 mg, 7.02 mmol) in THF/methanol (12 mL, 1:1). Yellow solid 170 mg (41%). ¹H NMR (601 MHz, DMSO-d₆) δ 12.90 (s, 1H), 8.33 (d, J=8.8 Hz, 2H), 8.22-8.09 (m, 2H), 7.40 (t, J=6.2 Hz, 1H), 3.64 (d, J=6.2 Hz, 2H), 3.55 (s, 2H), 3.18 (s, 2H).

Ethyl 2-({[(4-nitrophenyl)methyl](prop-2-yn-1-yl)carbamoyl}amino)acetate

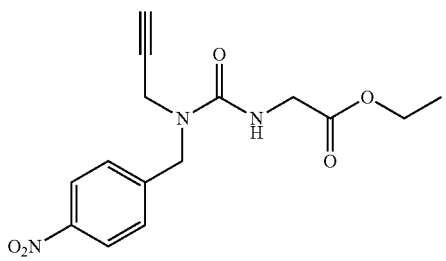 [SMILES: C#CCN(Cc1ccc([N+](=O)[O-])cc1)C(=O)NCC(=O)OCC]

The title compound was synthesized applying the general procedure 2 using [(4-nitrophenyl)methyl](prop-2-yn-1-yl)amine (480 mg, 2.52 mmol) and Ethyl isocyanatoacetate (0.28 mL, 2.5 mmol) in 10 mL of DCM. Red oil 800 mg (99%). LC-MS: Rt 5.4 min; m/z 320 [M+H]⁺. ¹H NMR (500 MHz, DMSO-d₆) δ 8.21 (m, 2H), 7.57-7.51 (m, 2H), 7.20 (t, J=5.8 Hz, 1H), 4.66 (s, 2H), 4.17-4.06 (m, 4H), 3.77 (d, J=5.8 Hz, 2H), 3.18 (t, J=2.4 Hz, 1H), 1.24-1.16 (m, 3H). ¹³C NMR (126 MHz, DMSO-d₆) δ 171.17, 157.54, 147.09, 146.81, 128.78 (2C), 123.87 (2C), 80.35, 75.24, 60.67, 49.29, 42.90, 36.34, 14.58.

Ethyl 2-({[(4-nitrophenyl)methyl](propyl)carbamoyl}amino)acetate

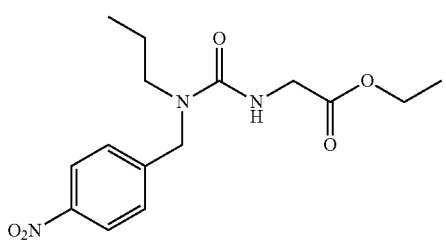 [SMILES: CCCN(Cc1ccc([N+](=O)[O-])cc1)C(=O)NCC(=O)OCC]

The title compound was synthesized applying the general procedure 2 using [(4-nitrophenyl)methyl](propyl)amine (600 mg, 3.09 mmol) and Ethyl isocyanatoacetate (0.35 mL, 3.09 mmol) in 10 mL of DCM. Yellow oil 990 mg (99%). LC-MS: Rt 5.8 min; m/z 346 [M-Na]⁺. ¹H NMR (400 MHz, DMSO-d₆) δ 8.24-8.16 (m, 2H), 7.52-7.46 (m, 2H), 6.94 (t, J=5.8 Hz, 1H), 4.58 (s, 2H), 4.09 (q, J=7.1 Hz, 2H), 3.76 (d, J=5.8 Hz, 2H), 3.17-3.09 (m, 2H), 1.49 (sxt, J=7.3 Hz, 2H), 1.20 (t, J=7.2 Hz, 3H), 0.81 (t, J=7.4 Hz, 3H). ¹³C NMR (126 MHz, DMSO-d₆) δ 171.45, 158.10, 148.25, 146.93, 128.57 (2C), 123.87 (2C), 60.62, 49.45, 48.54, 42.89, 21.46, 14.59, 11.41.

Ethyl 2-({[(4-nitrophenyl)methyl][(1H-1,2,3,4-tetrazol-5-yl)methyl]carbamoyl}amino)acetate

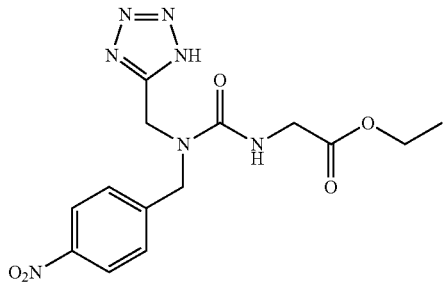 [SMILES: CCOC(=O)CNC(=O)N(Cc1ccc([N+](=O)[O-])cc1)Cc1nnn[nH]1]

To a 100 mL round-bottomed flask equipped with a stir bar was added Ethyl 2-{[(cyanomethyl)[(4-nitrophenyl)methyl]carbamoyl]amino}acetate (700 mg, 2.19 mmol), 12 mL of DMF, sodium azide (256 mg, 3.93 mmol), and ammonium chloride (222 mg, 4.15 mmol). The reaction vessel was stirred at 90° C. overnight (18 h). The reaction was cooled to RT and diluted with 50 mL of 1 M HCl (aq), then extracted with ethyl acetate (3×20 mL). The organic phase was collected, dried over magnesium sulfate and filtered, then evaporated to give the desired product. Brown oil 571 mg (72%). LC-MS: Rt 5.4 min; m/z 364 [M+H]$^+$. $^1$H NMR (500 MHz, DMSO-d$_6$) δ 16.23 (s, 1H), 8.24-8.19 (m, 2H), 7.56-7.51 (m, 2H), 7.31 (t, J=5.7 Hz, 1H), 4.75 (s, 2H), 4.72 (s, 2H), 4.09 (q, J=7.1 Hz, 2H), 3.77 (d, J=5.7 Hz, 2H), 1.18 (t, J=7.1 Hz, 3H). $^{13}$C NMR (126 MHz, DMSO-d$_6$) δ 171.11, 163.73, 162.75, 157.83, 146.94, 128.65 (2C), 124.17 (2C), 61.16, 50.07, 42.50, 36.25, 15.03.

Ethyl 2-({[(1-methyl-1H-1,2,3-triazol-4-yl)methyl][(4-nitrophenyl)methyl]carbamoyl}amino)acetate

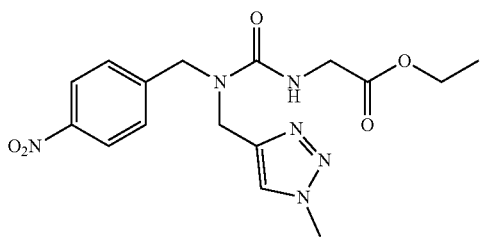 [SMILES: CCOC(=O)CNC(=O)N(Cc1ccc([N+](=O)[O-])cc1)Cc1cn(C)nn1]

To a solution of Iodomethane (0.2 mL, 433 mg, 3.05 mmol) in H$_2$O/DMF 1:4 (15 mL), NaN$_3$ (229 mg, 3.52 mmol), Na$_2$CO$_3$ (996 mg, 9.39 mmol), ascorbic acid (331 mg, 1.88 mmol), CuSO$_4$*5H$_2$O (235 mg, 0.95 mmol) and Ethyl 2-({[(4-nitrophenyl)methyl](prop-2-yn-1-yl)carbamoyl}amino)acetate (750 mg, 2.35 mmol) were added. The reaction mixture was stirred at RT overnight, diluted with a saturated solution of NH$_4$Cl (20 mL), treated with solid EDTA (1.0 g) and extracted with EtOAc (2×20 mL). The combined organic extracts were washed with H$_2$O (20 mL), dried over anhydrous MgSO$_4$, filtered, and concentrated under reduced pressure. The resulting residue was washed with hexane and dried under vacuum, to give the desired compound. Orange oil 860 mg (97%). LC-MS: Rt 5.4 min; m/z 377 [M+H]$^+$. $^1$H NMR (500 MHz, DMSO-d$_6$) δ 8.22-8.17 (m, 2H), 7.91 (s, 1H), 7.52-7.48 (m, 2H), 7.20 (t, J=5.8 Hz, 1H), 4.59 (s, 2H), 4.45 (s, 2H), 4.11 (q, J=7.1 Hz, 2H), 4.01 (s, 3H), 3.79 (d, J=5.8 Hz, 2H), 1.20 (t, J=7.1 Hz, 3H). $^{13}$C NMR (126 MHz, DMSO-d$_6$) δ 171.34, 162.76, 157.95, 147.02, 144.22, 128.71 (2C), 123.90 (2C), 60.67, 49.18, 42.95, 41.68, 36.68, 31.24, 14.57.

Ethyl 2-({[(2-methyl-2H-1,2,3,4-tetrazol-5-yl)methyl][(4-nitrophenyl)methyl]carbamoyl}amino)acetate

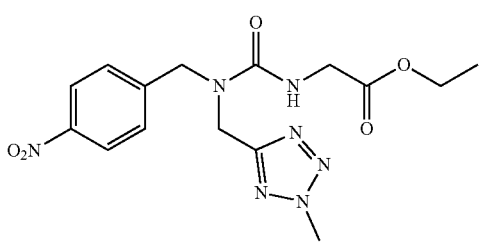 [SMILES: CCOC(=O)CNC(=O)N(Cc1ccc([N+](=O)[O-])cc1)Cc1nnn(C)n1]

The tetrazole derivative Ethyl 2-({[(4-nitrophenyl)methyl][(1H-1,2,3,4-tetrazol-5-yl)methyl]carbamoyl}amino)acetate (700 mg, 1.93 mmol) was dissolved in a solution of triethylamine (0.4 mL, 2.70 mmol) and acetonitrile (10 mL). The solution was heated to reflux temperature (90° C.), followed by the dropwise addition of Iodomethane (0.2 mL, 2.60 mmol). Upon completion, the solution was allowed to cool and stirred at room temperature for three days, then evaporated to dryness. The crude liquid containing a mixture of the 2- and 1-regioisomers was purified using silica gel chromatography (elution with DCM/MeOH) to give the desired 2-regioisomer. Brown oil 170 mg (23%). LC-MS: Rt 5.4 min; m/z 378 [M+H]$^+$. $^1$H NMR (601 MHz, DMSO-d$_6$) δ 8.21-8.19 (m, 2H), 7.53-7.49 (m, 2H), 7.25 (t, J=5.8 Hz, 1H), 4.72 (s, 2H), 4.68 (s, 2H), 4.31 (s, 3H), 4.09 (q, J=7.1 Hz, 2H), 3.77 (d, J=5.7 Hz, 2H), 1.19 (t, J=7.1 Hz, 3H). $^{13}$C NMR (151 MHz, DMSO-d$_6$) δ 171.30, 163.73, 162.76, 157.86, 147.23, 128.50 (2C), 123.91 (2C), 60.69, 49.70, 42.91, 36.25, 31.24, 14.56.

Ethyl 2-[({[1-(2-ethoxy-2-oxoethyl)-1H-1,2,3-triazol-4-yl]methyl}[(4-nitrophenyl)methyl]carbamoyl)amino]acetate

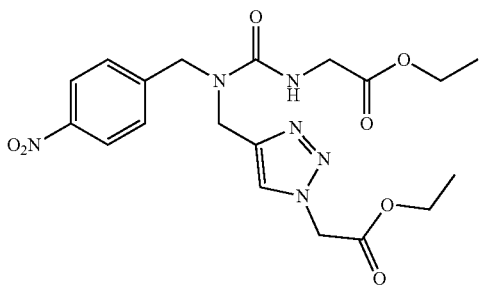 [SMILES: CCOC(=O)CNC(=O)N(Cc1ccc([N+](=O)[O-])cc1)Cc1cn(CC(=O)OCC)nn1]

The title compound was synthesized applying the general procedure 2 using ({[(4-nitrophenyl)methyl]amino}methyl)-1H-1,2,3-triazol-1-yl]acetate (350 mg, 1.1 mmol) and ethyl isocyanatoacetate (0.12 ml, 1.1 mmol) in 10 mL of DCM. Yellow oil 248 mg (50%). LC-MS: Rt 5.7 min; m/z 449 [M+H]$^+$. $^1$H NMR (601 MHz, DMSO-d$_6$) δ 8.19-8.17 (m, 2H), 7.97 (s, 1H), 7.96 (s, 1H), 7.48 (d, J=8.8 Hz, 2H), 5.36 (s, 2H), 4.61 (s, 2H), 4.50 (s, 2H), 4.18 (q, J=7.1 Hz, 2H), 4.09 (q, J=7.2 Hz, 2H), 3.77 (d, J=6.0 Hz, 2H), 1.23 (t, J=7.2 Hz, 3H), 1.19 (t, J=7.1 Hz, 3H)

Ethyl (2S)-2-({ethyl[(4-nitrophenyl)methyl]carbamoyl}amino)-4-(methylsulfanyl)butanoate

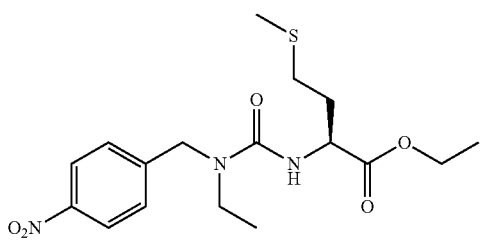

CDI (200 mg, 1.23 mg) was dissolved in DCM (10 mL). L-Methionine ethyl ester hydrochloride (263 mg, 1.23 mmol) and DIPEA (0.4 mL, 2.3 mmol) were added and stirred for 6 h at RT. Ethyl[(4-nitrophenyl)methyl]amine (200 mg, 1.11 mmol) in DCM (2 mL) was added and the mixture stirred at RT overnight. The solvent was removed in vacuo and the residue purified by column chromatography eluting DCM:MeOH. Yellow oil 400 mg (94%). LC-MS: Rt 6.0 min; m/z 384 [M+H]+. 1H NMR (601 MHz, DMSO-d6) δ 8.20 (d, J=8.8 Hz, 2H), 7.51-7.47 (m, 2H), 6.70 (d, J=7.9 Hz, 1H), 4.59 (s, 2H), 4.27 (td, J=7.9, 6.9 Hz, 1H), 4.10 (q, J=10.8 Hz, 1H), 4.09 (q, J=7.1 Hz, 1H), 3.27 (q, J=7.0 Hz, 2H), 2.51 (dt, J=3.6, 1.8 Hz, 2H), 2.04 (s, 3H), 1.99-1.92 (m, 2H), 1.19 (t, J=7.1 Hz, 3H), 1.03 (t, J=7.0 Hz, 3H). 13C NMR (126 MHz, DMSO-d6) δ 173.53, 157.74, 148.30, 128.61 (2C), 123.90 (2C), 60.75, 55.38, 53.39, 49.00, 41.51, 30.78, 30.55, 15.09, 14.58, 13.87.

3-{2-[2-(2-bromophenyl)pyrrolidin-1-yl]-2-oxo-ethyl}-1-[(4-nitrophenyl)methyl]-1-(prop-2-yn-1-yl)urea

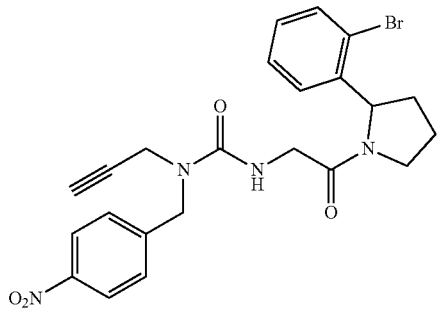 [SMILES: C#CCN(Cc1ccc([N+](=O)[O-])cc1)C(=O)NCC(=O)N1CCCC1c1ccccc1Br]

The title compound was synthesized applying the general procedure 3 using Ethyl 2-({[(4-nitrophenyl)methyl](prop-2-yn-1-yl)carbamoyl}amino)acetate (2100 mg, 6.58 mmol) and LiOH monohydrate (1380 mg, 32.88 mmol) in 16 mL of MeOH/THF 1:1, then 4 mL of water. The so-obtained carboxylic acid (1368 mg, 4.70 mmol) was then reacted with 2-(2-Bromophenyl)-pyrrolidine (905 mg, 4.00 mmol) HATU (2130 mg, 5.60 mmol) and DIPEA (1.05 mL, 6.00 mmol) in DMF (20 mL). Brown oil 1499 mg (46% over two steps). LC-MS: Rt 6.1 min; m/z 499 [M+H]+. 1H NMR (601 MHz, DMSO-d6) δ 8.20-8.15 (m, 2H), 7.55-7.50 (m, 2H), 7.32-7.23 (m, 2H), 7.20-7.10 (m, 2H), 6.77 (t, J=5.3 Hz, 1H), 4.65 (s, 2H), 4.08 (d, J=2.5 Hz, 2H), 3.97 (d, J=5.4 Hz, 2H), 3.94-3.87 (m, 1H), 3.66-3.58 (m, 2H), 3.17 (t, J=2.4 Hz, 1H), 2.30-2.23 (m, 1H), 1.98-1.90 (m, 1H), 1.84-1.66 (m, 2H). 13C NMR (126 MHz, DMSO-d6) δ 168.20, 157.50, 147.04, 142.38, 133.02, 128.99, 128.84, 128.81 (2C), 127.93, 127.26, 123.86 (2C), 121.83, 80.39, 75.27, 60.74, 49.45, 46.75, 43.49, 36.44, 32.29, 23.34.

3-{2-[2-(2-bromophenyl)pyrrolidin-1-yl]-2-oxo-ethyl}-1-[(4-nitrophenyl)methyl]-1-(prop-2-yn-1-yl)urea

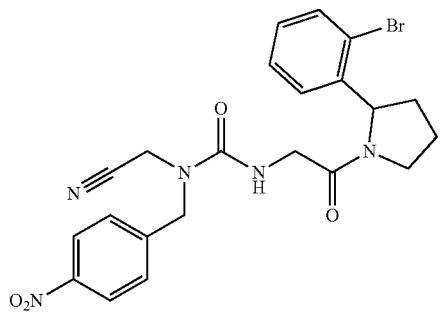 [SMILES: N#CCN(Cc1ccc([N+](=O)[O-])cc1)C(=O)NCC(=O)N1CCCC1c1ccccc1Br]

2-(2-Bromophenyl)-pyrrolidine (100 mg, 0.44 mmol, 1 equiv), 2-{[(cyanomethyl)[(4-nitrophenyl)methyl]carbamoyl]amino}acetic acid (142 mg, 0.49 mmol, 1.1 equiv) and HATU (235 mg, 0.62 mmol, 1.4 equiv) were dissolved in DMF (10 mL). DIPEA (0.12 mL, 0.66 mmol, 1.5 equiv) was added and the reaction mixture was stirred at room temperature overnight. After this time, the reaction mixture was diluted with EtOAc (40 mL) and washed with water (40 mL) and brine (40 mL). The organic layer was dried over MgSO4, filtered and concentrated in vacuo. (65 mg, 29%). Reaction was telescope to the final step.

3-{2-[2-(2-bromophenyl)pyrrolidin-1-yl]-2-oxo-ethyl}-1-[(1-methyl-1H-1,2,3-triazol-4-yl)methyl]-1-[(4-nitrophenyl)methyl]urea

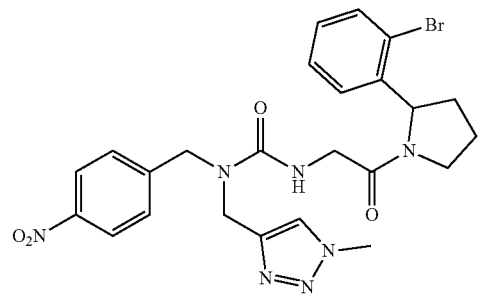 [SMILES: Cn1cc(CN(Cc2ccc([N+](=O)[O-])cc2)C(=O)NCC(=O)N2CCCC2c2ccccc2Br)nn1]

The title compound was synthesized applying the general procedure 3 using Ethyl 2-({[(1-methyl-1H-1,2,3-triazol-4-yl)methyl][(4-nitrophenyl)methyl]carbamoyl}amino)acetate (600 mg, 1.59 mmol) and LiOH monohydrate (334 mg, 7.97 mmol) in 8 mL of MeOH/THF 1:1, then 2 mL of water. The so-obtained carboxylic acid (254 mg, 0.73 mmol) was then reacted with 2-(2-Bromophenyl)-pyrrolidine (150 mg, 0.66 mmol), HATU (353 mg, 0.93 mmol) and DIPEA (0.17 mL, 1.00 mmol) in DMF (10 mL). Brown oil 311 mg (35% over two steps). LC-MS: Rt 5.9 min, m/z 556 [M+H]$^+$. $^1$H NMR (500 MHz, DMSO-d$_6$) δ 8.18-8.14 (m, 2H), 7.91 (s, 1H), 7.51-7.46 (m, 2H), 7.31-7.23 (m, 2H), 7.21-7.12 (m, 2H), 6.81 (t, J=5.4 Hz, 1H), 4.58 (s, 2H), 4.43 (s, 2H), 3.99 (d, J=5.4 Hz, 2H), 3.96 (s, 3H), 3.93-3.86 (m, 1H), 3.61 (qd, J=11.1, 10.3, 5.4 Hz, 2H), 232-2.27 (m, 2H), 1.98-1.66 (m, 2H). $^{13}$C NMR (126 MHz, DMSO-d$_6$) δ 169.44, 156.94, 147.65, 138.41, 137.91, 136.57, 132.88, 128.83, 128.04 (2C), 127.62, 125.34, 124.66, 124.42 (2C), 121.84, 64.96, 52.05, 46.78, 43.43, 42.85, 37.72, 32.46, 24.61.

3-{2-[2-(2-bromophenyl)pyrrolidin-1-yl]-2-oxo-ethyl}-1-[(2-methyl-2H-1,2,3,4-tetrazol-5-yl)methyl]-1-[(4-nitrophenyl)methyl]urea

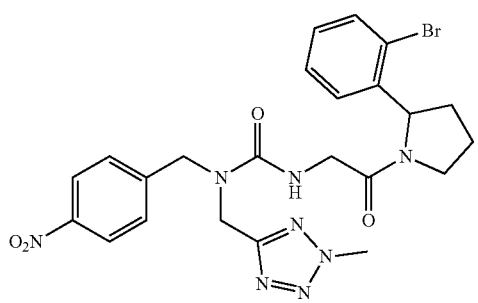 [SMILES: Cn1nnc(CN(Cc2ccc([N+](=O)[O-])cc2)C(=O)NCC(=O)N2CCCC2c2ccccc2Br)n1]

The title compound was synthesized applying the general procedure 3, using Ethyl 2-({[(2-methyl-2H-1,2,3,4-tetrazol-5-yl)methyl][(4-nitrophenyl)methyl]carbamoyl}amino)acetate (602 mg, 1.60 mmol), and LiOH monohydrate (335 mg, 7.98 mmol) in 8 mL of MeOH/THF 1:1, then 2 mL of water. The so-obtained carboxylic acid (255 mg, 0.73 mmol) was then reacted with 2-(2-Bromophenyl)-pyrrolidine (150 mg, 0.66 mmol) HATU (353 mg, 0.93 mmol) and DIPEA (0.17 mL, 1.00 mmol) in DMF (10 mL). Brown oil 221 mg (25% over two steps). LC-MS: Rt 5.9 min; m/z 558 [M+H]$^+$. $^1$H NMR (500 MHz, DMSO-d$_6$) δ 8.29-8.22 (m, 2H), 7.63-7.53 (m, 2H), 7.48-7.42 (m, 2H), 7.08-7.03 (m, 2H), 6.27 (s, 1H), 4.65 (s, 2H), 4.54 (s, 2H), 4.09 (s, 3H), 3.97 (d, J=5.2 Hz, 2H), 3.93-3.86 (m, 1H), 3.61-3.58 (m, 2H), 2.30-2.23 (m, 1H), 1.98-1.90 (m, 1H), 1.84-1.66 (m, 2H). $^{13}$C NMR (126 MHz, DMSO-d$_6$) δ 168.82, 157.22, 147.35, 140.39, 135.46, 132.78, 130.86, 128.82 (20), 127.98, 127.44, 125.00, 124.14 (20), 121.84, 70.11, 56.39, 48.11, 45.09, 43.17, 37.08, 32.37, 23.97.

Synthesis of Final Products

Ethyl 2-({[(4-aminophenyl)methyl](ethyl)carbamoyl}amino)acetate hydrochloride (12)

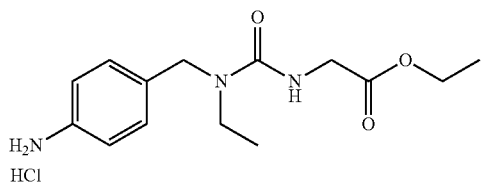 [SMILES: CCOC(=O)CNC(=O)N(CC)Cc1ccc(N)cc1 ; Cl]

The title compound was synthesized according to the general procedure 4, starting from Fe powder (235 mg, 4.21 mmol), calcium chloride (156 mg, 1.40 mmol), Ethyl 2-({ethyl[(4-nitrophenyl)methyl]carbamoyl}amino)acetate (434 mg, 1.40 mmol), in Ethanol/Water (12 mL, 10:2). The resultant oil was dissolved in a small amount of ethanol, to which 1.25 M HCl in ethanol was added. Evaporation of the solvent produced the title compound as yellow solid 145 mg (33%). Mp: 88-91° C. LC-MS: Rt=1.3 min, m/z 302 [M+Na]$^+$. $^1$H NMR (500 MHz, DMSO-d$_6$) δ 10.22 (bs, 2H), 7.38-7.31 (m, 4H), 6.91 (s, 1H), 4.45 (s, 2H), 4.09 (q, J=7.2 Hz, 2H), 3.76 (s, 2H), 3.19 (q, J=7.0 Hz, 2H), 1.20 (t, J=7.0 Hz, 3H), 1.01 (t, J=6.8 Hz, 3H). $^{13}$C NMR (126 MHz, DMSO-d$_6$) δ 171.62, 157.82, 139.80, 130.95, 128.81 (2C), 123.50 (2C), 60.57, 48.61, 42.86, 41.06, 14.60, 13.75. ESI+(m/z): [M+Na]$^+$ calculated for C$_{14}$H$_{21}$N$_3$O$_3$Na 302.1475; found 302.1460 [M+Na]$^+$. LC-MS purity: 96%

Ethyl 2-({[(4-aminophenyl)methyl](cyanomethyl)carbamoyl}amino)acetate hydrochloride (13)

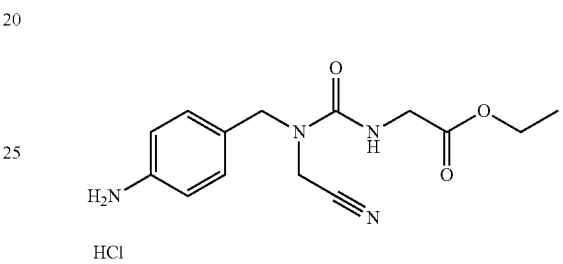

The title compound was synthesized according to the general procedure 4, starting from Fe powder (124 mg, 2.22 mmol), calcium chloride (82 mg, 0.74 mmol), Ethyl 2-{[(cyanomethyl)][(4-nitrophenyl)methyl]carbamoyl]amino}acetate (237 mg, 0.74 mmol), in Ethanol/Water (8 mL, 6:2). The resultant oil was dissolved in a small amount of ethanol, to which 1.25 M HCl in ethanol was added. Evaporation of the solvent produced the title compound as an orange solid 600 mg (25%). Mp: 91-95° C. LC-MS: Rt=1.3 min, m/z 314 [M+Na]$^+$. $^1$H NMR (500 MHz, DMSO-d$_6$) δ 9.73 (bs, 2H), 7.32 (d, J=8.3 Hz, 2H), 7.25 (d, J=8.0 Hz, 2H), 6.97 (t, J=7.9 Hz, 1H), 4.52 (s, 2H), 4.22 (s, 2H), 4.17-4.13 (m, 2H), 4.03 (d, J=7.9 Hz, 2H), 1.23-1.20 (m, 3H). $^{13}$C NMR (126 MHz, DMSO-d$_6$) δ 172.19, 170.08, 167.90, 156.09, 129.28 (4C), 122.40, 61.78, 43.56, 33.40, 25.86, 14.51. ESI+(m/z): [M+Na]$^+$ calculated for C$_{14}$H$_{19}$N$_4$O$_3$Na 314.1349; found 314.1360 [M+Na]$^+$. LC-MS purity: 95%.

Ethyl 2-({[(4-aminophenyl)methyl][(1H-1,2,3,4-tetrazol-5-yl)methyl]carbamoyl}amino)acetate hydrochloride (14)

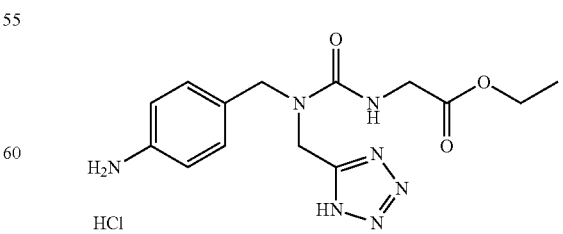

The title compound was synthesized according to the general procedure 4, starting from Fe powder (263 mg, 4.71 mmol), calcium chloride (174 mg, 1.57 mmol), Ethyl 2-({

[(4-nitrophenyl)methyl][(1H-1,2,3,4-tetrazol-5-yl)methyl] carbamoyl}amino)acetate (570 mg, 1.57 mmol), in Ethanol/Water (12 mL, 10:2). The resultant oil was dissolved in a small amount of ethanol, to which 1.25 M HCl in ethanol was added. Evaporation of the solvent produced the title compound as an orange solid 145 mg (25%). Mp: 146-149° C. LC-MS: Rt=1.4 min, m/z 334 [M+H]$^+$. $^1$H NMR (500 MHz, DMSO-d$_6$) δ 10.05 (bs, 2H), 7.37-7.26 (m, 5H), 4.66 (s, 2H), 4.56 (s, 2H), 4.07 (q, J=6.7 Hz, 2H), 3.76 (d, J=5.2 Hz, 2H), 1.05 (t, J=6.8 Hz, 3H). $^{13}$C NMR (126 MHz, DMSO-d$_6$) δ 171.18, 157.88, 147.54, 128.93 (4C), 122.94 (2C), 60.70, 56.49, 49.70, 42.91, 14.61. ESI+(m/z): [M+H]$^+$ calculated for $C_{14}H_{19}N_7O_3$ 333.1543; found 333.1550 [M+H]$^+$. LC-MS purity: 100%.

Ethyl (2S)-2-({[(4-aminophenyl)methyl](ethyl) carbamoyl}amino)-4-(methylsulfanyl)butanoate hydrochloride (15)

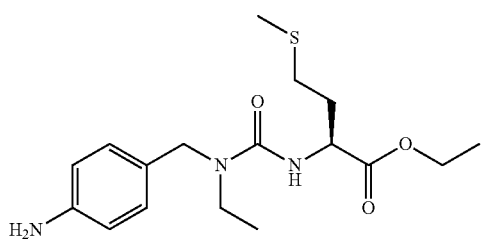

The title compound was synthesized according to the general procedure 4, starting from Fe powder (124 mg, 2.22 mmol), calcium chloride (82 mg, 0.74 mmol), Ethyl 2-{[(cyanomethyl)[(4-nitrophenyl)methyl]carbamoyl] amino}acetate (237 mg, 0.74 mmol), in Ethanol/Water (8 mL, 6:2). The resultant oil was dissolved in a small amount of ethanol, to which 1.25 M HCl in ethanol was added. Evaporation of the solvent produced the title compound as an orange solid 145 mg (42%). LC-MS: Rt=5.2 min, m/z 376 [M+Na]$^+$. $^1$H NMR (500 MHz, DMSO-d$_6$) δ 10.38 (bs, 2H), 7.49-7.25 (m, 4H), 6.73-6.56 (m, 1H), 5.38 (bs, 2H), 4.81-4.67 (m, 1H), 4.47 (s, 2H), 4.44-4.32 (m, 2H), 4.31-4.19 (m, 2H), 4.16-3.98 (m, 2H), 3.29-3.06 (m, 2H) 2.04 (s, 2H), 2.01-1.90 (m, 1H), 1.19 (t, J=7.1 Hz, 3H), 1.00 (t, J=7.0 Hz, 3H). $^{13}$C NMR (126 MHz, DMSO-d$_6$) δ 206.95, 173.6, 158.00, 157.74, 139.97, 130.79, 128.85 (2C), 123.64 (2C), 60.71, 53.38, 31.17, 30.79, 30.58, 15.11, 14.60, 13.80. LC-MS purity: 100%.

Ethyl 2-({[(4-aminophenyl)methyl](propyl) carbamoyl}amino)acetate (16)

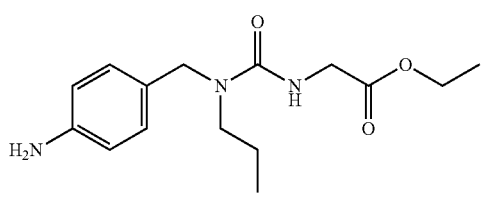 [SMILES: CCCN(Cc1ccc(N)cc1)C(=O)NCC(=O)OCC]

The title compound was synthesized according to the general procedure 4, starting from Fe powder (503 mg, 9.00 mmol), calcium chloride (333 mg, 3.00 mmol), Ethyl 2-({[(4-nitrophenyl)methyl](propyl)carbamoyl}amino)acetate (970 mg, 3.00 mmol), in Ethanol/Water (24 mL, 20:4). Yellow oil 550 mg (62%). LC-MS: Rt=4.7 min, m/z 316 [M+Na]$^+$. $^1$H NMR (500 MHz, DMSO-d$_6$) δ 6.92-6.89 (m, 2H), 6.72 (t, J=5.6 Hz, 1H), 6.52-6.49 (m, 2H), 4.24 (s, 2H), 4.09 (q, J=7.1 Hz, 2H), 3.76 (d, J=5.8 Hz, 2H), 3.03-2.97 (m, 2H), 1.49 (h, J=7.3 Hz, 2H), 1.20 (t, J=7.2 Hz, 3H), 0.81 (t, J=7.4 Hz, 3H). $^{13}$C NMR (126 MHz, DMSO-d$_6$) δ 171.66, 157.97, 147.90, 128.65 (2C), 126.10, 114.38 (2C), 60.77, 49.02, 47.26, 42.76, 21.13, 14.80, 11.54. ESI+(m/z): [M+Na]$^+$ calculated for $C_{15}H_{23}N_3O_3Na$ 316.1631; found 316.1614 [M+Na]$^+$. LC-MS purity: 99%

Ethyl 2-({[(4-aminophenyl)methyl](cyclopropylmethyl)carbamoyl}amino)acetate hydrochloride (17)

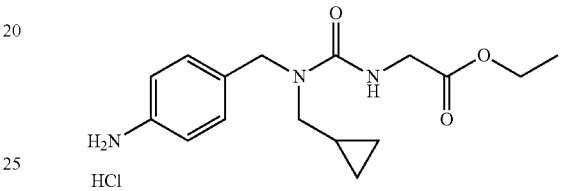

The title compound was synthesized according to the general procedure 4, starting from Fe powder (75 mg, 1.34 mmol), calcium chloride (50 mg, 0.45 mmol), Ethyl 2-{[(cyclopropylmethyl)[(4-nitrophenyl)methyl]carbamoyl] amino}acetate (150 mg, 0.45 mmol), in Ethanol/Water (8 mL, 6:2). The resultant oil was dissolved in a small amount of ethanol, to which 1.25 M HCl in ethanol was added. Evaporation of the solvent produced the title compound as an orange solid 150 mg (98%). Mp: 101-105° C. LC-MS: Rt=4.8 min, m/z 328 [M+Na]$^+$. $^1$H NMR (500 MHz, DMSO-d$_6$) δ 10.32 (bs, 2H), 7.37-7.31 (m, 4H), 6.94 (s, 1H), 4.56 (s, 2H), 4.09 (q, J=7.1 Hz, 2H), 3.75 (s, 2H), 3.07 (d, J=6.8 Hz, 2H), 2.88 (dd, J=6.7, 1.4 Hz, 1H), 1.20 (t, J=6.7 Hz, 3H), 0.39-0.35 (m, 2H), 0.18-0.10 (m, 2H). $^{13}$C NMR (126 MHz, DMSO-d$_6$) δ 171.52, 158.08, 139.79, 128.76, 128.70 (2C), 123.54 (2C), 60.58, 50.51, 49.12, 42.91, 14.60, 10.55, 3.75, 3.44. ESI+(m/z): [M+Na]$^+$ calculated for $C_{16}H_{23}N_3O_3Na$ 328.1631; found 328.1650 [M+Na]$^+$. LC-MS purity: 99%.

Ethyl 2-({[(4-aminophenyl)methyl][(1-methyl-1H-1,2,3-triazol-4-yl)methyl]carbamoyl}amino)acetate hydrochloride (18)

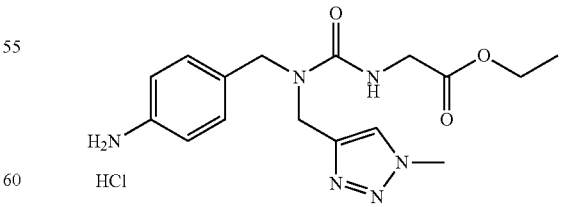

The title compound was synthesized according to the general procedure 4, starting from Fe powder (85 mg, 1.51 mmol), calcium chloride (56 mg, 0.50 mmol), Ethyl 2-({[(1-methyl-1H-1,2,3-triazol-4-yl)methyl][(4-nitrophenyl) methyl]carbamoyl}amino)acetate (190 mg, 0.50 mmol), in Ethanol/Water (8 mL, 6:2). The resultant oil was dissolved in a small amount of ethanol, to which 1.25 M HCl in ethanol was added. Evaporation of the solvent produced the title compound as an orange solid 155 mg (80%). Mp: 144-147° C. LC-MS: Rt=1.2 min, m/z 369 [M+Na]⁺. ¹H NMR (500 MHz, DMSO-d₆) δ 10.29 (bs, 2H), 7.87 (s, 1H), 7.41-7.30 (m, 4H), 7.18 (s, 1H), 4.47 (s, 2H), 4.39 (s, 2H), 4.13-4.07 (m, 2H), 4.01 (s, 3H), 3.78 (s, 2H), 1.23-1.17 (m, 3H). ¹³C NMR (126 MHz, DMSO-d₆) δ 171.41, 157.94, 144.36, 138.82, 130.99, 129.01 (2C), 124.60, 123.62 (2C), 60.64, 56.48, 48.74, 42.94, 36.70, 14.60. ESI+(m/z): [M+Na]⁺ calculated for $C_{16}H_{22}N_6O_3Na$ 369.1645; found 369.1650 [M+Na]⁺. LC-MS purity: 95%.

Ethyl 2-({[(4-aminophenyl)methyl][(2-methyl-2H-1, 2,3,4-tetrazol-5-yl)methyl]carbamoyl}amino)acetate hydrochloride (19)

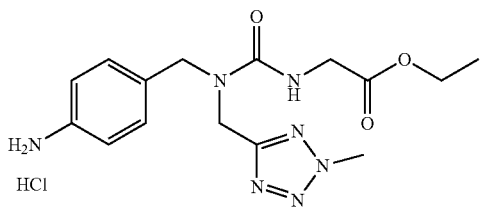 [SMILES: Cl ; CCOC(=O)CNC(=O)N(Cc1ccc(N)cc1)Cc1nnn(C)n1]

The title compound was synthesized according to the general procedure 4, starting from Fe powder (67 mg, 1.19 mmol), calcium chloride (44 mg, 0.40 mmol), Ethyl 2-({[(2-methyl-2H-1,2,3,4-tetrazol-5-yl)methyl][(4-nitrophenyl)methyl]carbamoyl}amino)acetate (150 mg, 0.40 mmol), in Ethanol/Water (8 mL, 6:2). The resultant oil was dissolved in a small amount of ethanol, to which 1.25 M HCl in ethanol was added. Evaporation of the solvent produced the title compound as an orange solid 50 mg (33%). Mp: 128-131° C. LC-MS: Rt=2.9 min, m/z 370 [M+Na]⁺. ¹H NMR (400 MHz, DMSO-d₆) δ 9.87 (bs, 2H), 7.37-7.31 (m, 2H), 7.31-7.25 (m, 2H), 7.23 (t, J=5.5 Hz, 1H), 4.64 (s, 2H), 4.53 (s, 2H), 4.32 (s, 3H), 4.09 (q, J=7.1 Hz, 2H), 3.77 (d, J=5.5 Hz, 2H), 1.20 (t, J=7.1 Hz, 3H). ¹³C NMR (126 MHz, DMSO-d₆) δ 169.32, 158.73, 156.94, 144.54, 128.55 (2C), 126.17 (2C), 117.15, 61.61, 52.05, 43.44, 41.86, 32.67, 14.60. ESI+(m/z): [M+Na]⁺ calculated for $C_{15}H_{21}N_7O_3Na$ 370.1598; found 370.1600 [M+Na]⁺. LC-MS purity: 95%.

({[(4-aminophenyl)methyl]({[1-(2-ethoxyprop-2-en-1-yl)-1H-1,2,3-triazol-4-yl]methyl}) carbamoyl}amino)acetate hydrochloride (20)

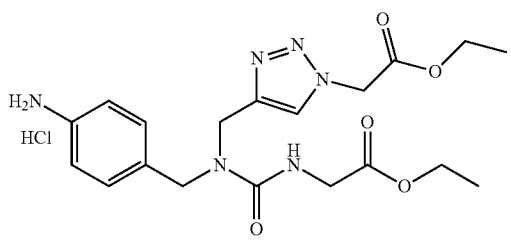 [SMILES: Cl ; CCOC(=O)CNC(=O)N(Cc1ccc(N)cc1)Cc1cn(CC(=O)OCC)nn1]

The title compound was synthesized according to general procedure 4, starting from Fe powder (92 mg, 1.64 mmol), calcium chloride (61 mg, 0.55 mmol), ethyl 2-[({[1-(2-ethoxy-2-oxoethyl)-1H-1,2,3-triazol-4-yl]methyl}[(4-nitrophenyl)methyl]carbamoyl)amino]acetate (245 mg, 0.55 mmol), in Ethanol/Water (8 mL, 3:1). The resultant oil was dissolved in a small amount of ethanol, to which 1.25 M HCl in ethanol was added. Evaporation of the solvent produced the title compound as an orange solid. 98 mg (39%). LC-MS: Rt=4.7 min, m/z 419 [M+H]⁺. ¹H NMR (500 MHz, DMSO-d₆) δ 10.30 (s, 2H), 7.99 (s, 1H), 7.41-7.27 (m, 4H), 7.21 (s, 1H), 5.38 (s, 2H), 4.86 (bs, 2H), 4.48 (s, 2H), 4.42 (s, 2H), 4.19 (q, J=7.2 Hz, 2H), 4.10 (q, J=7.1 Hz, 2H), 3.82-3.75 (m, 2H), 1.23 (t, J=7.1 Hz, 3H), 1.19 (t, J=7.2 Hz, 3H). ¹³C NMR (126 MHz, DMSO-d₆) δ 171.4, 167.7, 157.9, 144.3, 129.0 (2C), 125.1, 123.6 (2C), 61.9, 60.6, 50.8, 48.8, 43.0, 41.9, 41.2, 35.5, 14.6, 14.4. LC-MS purity: 80%.

Ethyl 2-({[(4-aminophenyl)methyl][1-(carbamoylmethyl)-1H-1,2,3-triazol-4-yl]carbamoyl}amino)acetate (21)

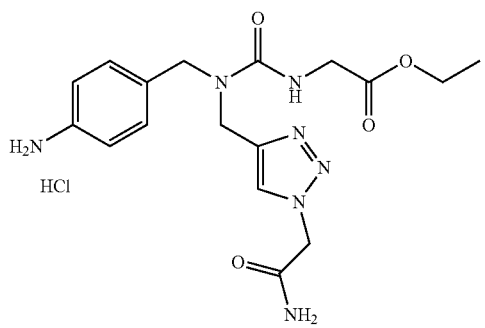 [SMILES: CCOC(=O)CNC(=O)N(Cc1ccc(N)cc1)Cc1cn(CC(N)=O)nn1 ; Cl]

The title compound was synthesized according to the general procedure 4, starting from Fe powder (60 mg, 1.07 mmol), calcium chloride (40 mg, 0.36 mmol), Ethyl 2-[({[1-(carbamoylmethyl)-1H-1,2,3-triazol-4-yl]methyl}[(4-nitrophenyl)methyl]carbamoyl)amino]acetate (150 mg, 0.36 mmol), in Ethanol/Water (8 mL, 6:2). The resultant oil was dissolved in a small amount of ethanol, to which 1.25 M HCl in ethanol was added. Evaporation of the solvent produced the title compound as an orange solid which was recrystalised from diethylether 60 mg (39%). LC-MS: Rt=9.0 min, m/z 413 [M+Na]⁺. ¹H NMR (500 MHz, DMSO-d₆) δ 10.17 (bs, 1H), 8.94-8.62 (m, 2H), 8.34-8.16 (m, 2H), 8.00-7.66 (m, 1H), 7.44-7.20 (m, 1H), 5.04 (s, 2H), 4.40-4.22 (m, 1H), 4.03 (s, 2H), 3.88-3.60 (m, 2H), 3.53-2.99 (m, 4H), 2.80 (s, 2H), 1.27-1.11 (m, 3H). ¹³C NMR (126 MHz, DMSO-d₆) δ 167.67, 158.05, 144.33, 129.00 (2C), 125.28, 123.29 (2C), 61.70, 60.67, 50.75, 48.69, 42.77, 41.22, 35.49, 31.64, 19.45.

Ethyl 2-({[(4-aminophenyl)methyl](prop-2-yn-1-yl)carbamoyl}amino)acetate (22)

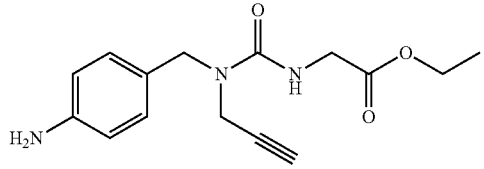 [SMILES: C#CCN(Cc1ccc(N)cc1)C(=O)NCC(=O)OCC]

The title compound was synthesized according to the general procedure 4, starting from Fe powder (487 mg, 8.73 mmol), calcium chloride (323 mg, 2.91 mmol), Ethyl 2-({[(4-nitrophenyl)methyl](prop-2-yn-1-yl)carbamoyl}amino)acetate (929 mg, 2.91 mmol), in Ethanol/Water (24 mL, 20:4). Yellow oil 350 mg (42%). LC-MS: Rt=4.3 min, m/z 312 [M+Na]$^+$. $^1$H NMR (500 MHz, DMSO-d$_6$) δ 7.40-7.37 (m, 2H), 7.36-7.33 (m, 2H), 7.19 (t, J=6.0 Hz, 1H), 4.54 (s, 2H), 4.10 (q, J=7.1 Hz, 1H), 4.02 (d, J=2.5 Hz, 2H), 3.77 (d, J=5.9 Hz, 2H), 3.18 (t, J=2.4 Hz, 1H), 1.20 (t, J=7.1 Hz, 3H). $^{13}$C NMR (126 MHz, DMSO-d$_6$) δ 171.26, 157.55, 138.24, 131.25, 128.90 (2C), 123.59 (2C), 80.43, 75.02, 60.65, 48.91, 42.90, 35.79, 14.60. ESI+(m/z): [M+Na]$^+$ calculated for C$_{15}$H$_{19}$N$_3$O$_3$Na 312.1318; found 312.1316 [M+Na]$^+$. LC-MS purity: 95%

Ethyl 2-{[ethyl({[(1R,9S,10S)-10-hydroxy-12-oxa-8-azatricyclo[7.3.1.0$^{2,7}$]trideca-2,4,6-trien-4-yl]methyl})carbamoyl]amino}acetate hydrochloride (23)

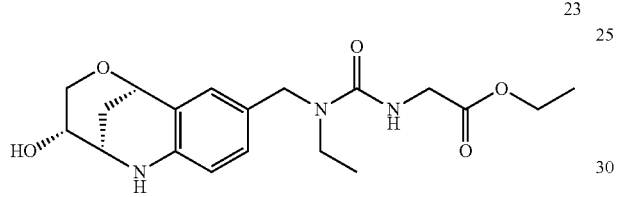

The title compound was synthesized according to the general procedure 2, starting from (1R,9S,10S)-4-[(ethylamino)methyl]-12-oxa-8-azatricyclo[7.3.1.0$^{2,7}$]trideca-2,4,6-trien-10-ol (187 mg, 0.75 mmol), and Ethyl isocyanatoacetate (97 mg, 0.75 mmol) in DCM. The crude product was purified by column chromatography (DCM/MeOH). The product of which was dissolved in EtOH and HCl 1M in ethanol added. The volatiles were removed and the solid dissolved in water and washed with DCM before freeze drying to a dark solid 50 mg (16%). $^1$H NMR (400 MHz, DMSO-d$_6$) δ 10.10 (bs, 1H), $^1$H NMR (500 MHz, DMSO-d$_6$) δ 9.11 (d, J=8.6 Hz, 1H), 8.38-8.02 (m, 1H), 7.77-7.55 (m, 1H), 7.18-6.91 (m, 1H), 6.68-6.46 (m, 1H), 6.27 (s, 2H), 5.23 (d, J=33.4 Hz, 2H), 4.64-4.40 (m, 2H), 4.29-3.97 (m, 4H), 3.83-3.76 (m, 3H), 3.67-3.59 (m, 4H), 3.11-3.05 (m, 4H), 2.99-2.89 (m, 4H).

1-[(4-aminophenyl)methyl]-3-{2-[2-(phenyl)pyrrolidin-1-yl]-2-oxoethyl}-1-ethylurea (9)

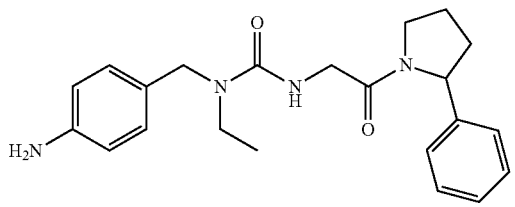 [SMILES: CCN(Cc1ccc(N)cc1)C(=O)NCC(=O)N1CCCC1c1ccccc1]

3-{2-[2-(2-bromophenyl)pyrrolidin-1-yl]-2-oxoethyl}-1-ethyl-1-[(4-nitrophenyl)methyl]urea (100 mg, 0.2 mmol) and ammonium formate (90 mg, 1.4 mmol) were dissolved in THF/MeOH (5 mL, 1:4). Pd/C 10% (22 mg, 0.2 mmol) was added and the mixture stirred at RT overnight. The solution was filtered on a celite pad and concentrated to yield an oil. This was dissolved in DCM and washed with water. The organic phase was collected dried over MgSO$_4$, filtered and concentrated yielding a yellow solid. 58 mg, (75%). $^1$H NMR (500 MHz, DMSO-d$_6$) δ $^1$H NMR (500 MHz, DMSO-d$_6$) δ 7.38 (t, J=7.6 Hz, 1H), 7.28 (ddd, J=7.8, 5.9, 1.6 Hz, 1H), 7.25-7.21 (m, 2H), 7.20-7.11 (m, 1H), 6.90 (dd, J=9.6, 8.3 Hz, 1H), 6.48 (d, J=8.1 Hz, 2H), 6.18 (dq, J=49.3, 5.2 Hz, 1H), 5.17-5.03 (m, 1H), 4.93 (s, 1H), 4.30-4.09 (m, 2H), 4.02-3.84 (m, 1H), 3.78 (ddd, J=9.9, 8.1, 3.3 Hz, 1H), 3.68-3.51 (m, 1H), 3.15-3.03 (m, 1H), 2.41-2.30 (m, 1H), 2.21 (dddd, J=12.2, 10.8, 8.1, 6.8 Hz, 1H), 1.91 (dtt, J=14.1, 7.2, 3.7 Hz, 1H), 1.86-1.76 (m, 2H), 1.72 (ddt, J=12.2, 6.1, 2.9 Hz, 1H), 1.14 (td, J=7.1, 2.1 Hz, 1H), 0.95 (dt, J=12.5, 7.0 Hz, 3H). $^{13}$C NMR (126 MHz, DMSO-d$_6$) δ $^{13}$C NMR (126 MHz, DMSO-d$_6$) δ $^{13}$C NMR (126 MHz, DMSO-d$_6$) δ 169.06, 157.69, 128.83 (2C), 128.78 (2C), 128.49 (2C), 125.99 (2C), 114.26, 60.55, 48.70, 47.35, 46.35, 43.37, 40.52, 36.54, 34.06, 23.61, 21.60, 13.56.

1-[(4-aminophenyl)methyl]-3-{2-[2-(2-bromophenyl)pyrrolidin-1-yl]-2-oxoethyl}-1-ethylurea hydrochloride (10)

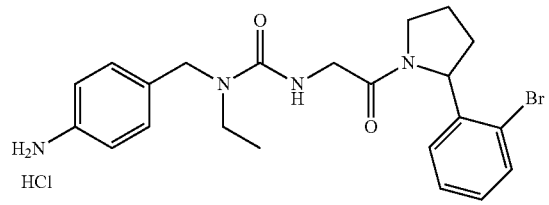 [SMILES: Cl ; CCN(Cc1ccc(N)cc1)C(=O)NCC(=O)N1CCCC1c1ccccc1Br]

The title compound was synthesized according to general procedure 4, starting from Fe powder (34 mg, 0.61 mmol), calcium chloride (23 mg, 0.2 mmol), 3-{2-[2-(2-bromophenyl)pyrrolidin-1-yl]-2-oxoethyl}-1-ethyl-1-[(4-nitrophenyl)methyl]urea (245 mg, 0.55 mmol), in Ethanol/Water (8 mL, 3:1). The resultant oil was dissolved in a small amount of ethanol, to which 1.25 M HCl in ethanol was added. Evaporation of the solvent produced the title compound as an orange solid. 40 mg (39%). LC-MS: Rt=5.5 min, m/z 459 [M+H]$^+$. $^1$H NMR (500 MHz, DMSO-d$_6$) δ 10.30 (s, 1H) 7.68 (d, J=7.8 Hz, 2H), 7.60 (d, J=7.8 Hz, 2H), 7.50-7.34 (m, 1H), 7.34-7.25 (m, 1H), 7.25-7.11 (m, 1H), 7.04 (d, J=8.0 Hz, 1H), 6.38 (s, 1H), 5.23-5.14 (m, 2H), 4.52 (d, J=23.1 Hz, 2H), 4.35 (d, J=22.5 Hz, 2H), 4.03-3.87 (m, 2H), 3.68-3.54 (m, 2H), 3.18-3.10 (m, 1H), 2.26 (dtd, J=11.5, 7.7, 3.6 Hz, 1H), 2.01-1.91 (m, 1H), 1.90-1.77 (m, 1H), 1.74-1.66 (m, 1H), 1.06-0.91 (m, 4H). $^{13}$C NMR (126 MHz, DMSO-d$_6$) δ 168.69, 157.78, 142.44, 133.48, 133.03, 128.92, 127.95, 127.29, 125.58, 121.85, 60.73, 47.70, 46.74, 43.35, 34.56, 32.28, 23.36, 13.70.

1-[(4-aminophenyl)methyl]-3-{2-[2-(2-bromophenyl)pyrrolidin-1-yl]-2-oxoethyl}-1-(cyclopropylmethyl)urea (11)

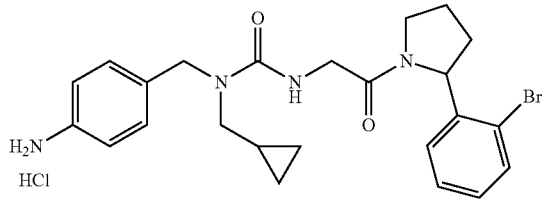 [SMILES: Cl ; Nc1ccc(CN(CC2CC2)C(=O)NCC(=O)N2CCCC2c2ccccc2Br)cc1]

The title compound was synthesized according to general procedure 4, starting from Fe powder (34 mg, 0.61 mmol), calcium chloride (23 mg, 0.2 mmol), 3-{2-[2-(2-bromophenyl)pyrrolidin-1-yl]-2-oxoethyl}-1-(cyclopropylmethyl)-1-[(4-nitrophenyl)methyl]urea (105 mg, 0.0.2 mmol), in Ethanol/Water (8 mL, 3:1). The resultant oil was dissolved in a small amount of ethanol, to which 1.25 M HCl in ethanol was added. Evaporation of the solvent produced the title compound as an orange solid. 60 mg (56%). LC-MS: Rt=5.5 min, m/z 487 [M+2H]$^+$. $^1$H NMR (500 MHz, DMSO-d$_6$) δ 9.54 (s, 1H) 8.23-8.12 (m, 1H), 8.05 (ddd, J=8.4, 5.3, 2.9 Hz, 1H), 7.67 (d, J=8.0 Hz, 2H), 7.60 (d, J=7.9 Hz, 2H), 5.92 (s, 1H), 5.20 (t, J=7.1 Hz, 2H), 4.69-4.49 (m, 2H), 4.00-3.78 (m, 4H), 3.73 (ddd, J=11.7, 8.1, 3.1 Hz, 1H), 3.61 (dtd, J=27.2, 10.5, 10.1, 7.4 Hz, 2H), 3.08 (dq, J=29.9, 6.5 Hz, 3H), 2.84 (dd, J=41.7, 6.7 Hz, 2H), 2.32-2.23 (m, 1H), 1.94 (ddq, J=14.1, 7.0, 3.5 Hz, 2H), 1.86-1.63 (m, 1H), 1.02-0.90 (m, 1H), 0.44-0.27 (m, 2H).

1-[(4-aminophenyl)methyl]-3-{2-[2-(2-bromophenyl)pyrrolidin-1-yl]-2-oxoethyl}-1-(prop-2-yn-1-yl)urea hydrochloride (1)

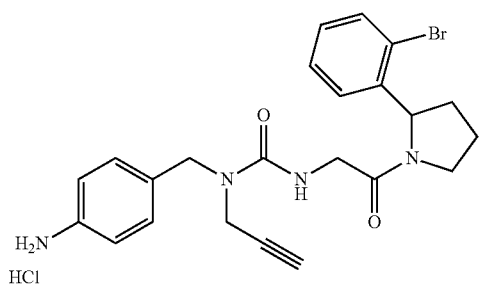 [SMILES: C#CCN(Cc1ccc(N)cc1)C(=O)NCC(=O)N1CCCC1c1ccccc1Br ; Cl]

The title compound was synthesized according to the general procedure 4, starting from Fe powder (502 mg, 8.99 mmol), calcium chloride (333 mg, 3.00 mmol), 3-{2-[2-(2-bromophenyl)pyrrolidin-1-yl]-2-oxoethyl}-1-[(4-nitrophenyl)methyl]-1-(prop-2-yn-1-yl)urea (1496 mg, 3.00 mmol), in Ethanol/Water (24 mL, 20:4). The resultant oil was dissolved in a small amount of ethanol, to which 1.25 M HCl in ethanol was added. Evaporation of the solvent produced the title compound as an orange solid 600 mg (40%). Mp: 136-140° C. LC-MS: Rt=5.3 min, m/z 469 [M+H]$^+$. $^1$H NMR (500 MHz, DMSO-d$_6$) δ 10.28 (s, 2H), 7.60 (ddd, J=7.9, 2.6, 1.2 Hz, 1H), 7.37 (dd, J=8.6, 2.1 Hz, 2H), 7.35-7.24 (m, 3H), 7.16 (dddd, J=12.6, 9.4, 7.6, 1.7 Hz, 2H), 6.71 (s, 1H), 5.22-5.16 (m, 1H), 4.53 (s, 2H), 4.02 (d, J=2.4 Hz, 2H), 4.00-3.94 (m, 2H), 3.90 (tdd, J=7.7, 4.6, 2.3 Hz, 1H), 3.60 (dtd, J=16.7, 9.6, 7.7 Hz, 1H), 3.16 (dt, J=7.3, 2.4 Hz, 1H), 2.26 (tdd, J=11.8, 9.7, 6.8 Hz, 1H), 1.95 (tq, J=10.4, 3.6 Hz, 1H), 1.80-1.73 (m, 1H), 1.68 (ddt, J=13.6, 10.2, 6.2 Hz, 1H). $^{13}$C NMR (126 MHz, DMSO-d$_6$) δ 168.25, 157.49, 142.39, 138.47, 133.47, 133.02, 131.11, 129.81, 129.02 (2C), 127.95, 127.27, 123.60 (2C), 80.47, 75.02, 60.72, 56.48, 49.00, 43.47, 35.97, 32.28, 24.61. ESI+(m/z): [M+H]$^+$ calculated for C$_{23}$H$_{25}$$^{79}$BrN$_4$O$_2$ 468.1161; found 468.1193 [M+H]$^+$; calculated for C$_{23}$H$_{25}$$^{81}$BrN$_4$O$_2$ (97.3%) 470.1140; found 470.1147 [M+H]$^+$. LC-MS purity: 100%.

3-{2-[2-(2-bromophenyl)pyrrolidin-1-yl]-2-oxoethyl}-1-(cyanomethyl)-1-[(4-nitrophenyl)methyl]urea (2)

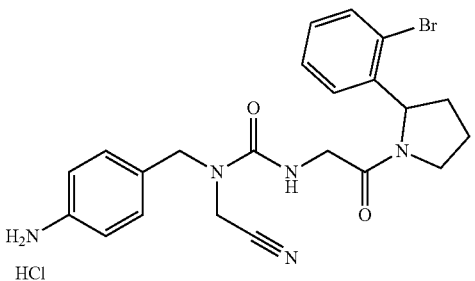 [SMILES: N#CCN(Cc1ccc(N)cc1)C(=O)NCC(=O)N1CCCC1c1ccccc1Br ; Cl]

The title compound was synthesized according to the general procedure 4, starting from Fe powder (20 mg, 0.36 mmol), calcium chloride (13 mg, 0.12 mmol), 3-{2-[2-(2-bromophenyl)pyrrolidin-1-yl]-2-oxoethyl}-1-[(4-nitrophenyl)methyl]-1-(prop-2-yn-1-yl)urea (60 mg, 0.12 mmol), in Ethanol/Water (8 mL, 6:2). The resultant oil was dissolved in a small amount of ethanol, to which 1.25 M HCl in ethanol was added. Evaporation of the solvent produced the title compound as an orange solid which was recrystallized from acetone 50 mg (82%). $^1$H NMR (500 MHz, DMSO-d$_6$) δ 10.06 (s, 1H), 7.67 (dd, J=7.9, 1.2 Hz, 1H), 7.60 (dd, J=7.9, 1.3 Hz, 2H), 7.34 (d, J=8.4 Hz, 2H), 7.21-7.11 (m, 2H), 6.79 (d, J=8.5 Hz, 2H), 5.28-5.19 (m, 2H), 3.90-3.79 (m, 2H), 3.59 (td, J=9.7, 7.0 Hz, 2H), 2.33-2.18 (m, 2H), 2.02-1.58 (m, 5H). $^{13}$C NMR (126 MHz, DMSO-d$_6$) δ $^{13}$C NMR (126 MHz, DMSO-d$_6$) δ 206.95, 168.29, 158.37, 142.34, 129.05, 128.64, 127.98, 127.26, 123.29, 121.82, 121.58, 60.72, 60.27, 47.68, 46.62, 42.82, 40.52, 34.45, 32.34, 31.17, 23.30, 21.23.

1-[(4-aminophenyl)methyl]-3-{2-[2-(2-bromophenyl)pyrrolidin-1-yl]-2-oxoethyl}-1-[(1-methyl-1H-1,2,3-triazol-4-yl)methyl]urea hydrochloride (3)

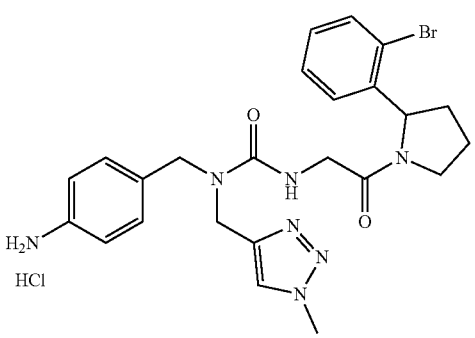 [SMILES: Cl ; Cn1cc(CN(Cc2ccc(N)cc2)C(=O)NCC(=O)N2CCCC2c2ccccc2Br)nn1]

The title compound was synthesized according to the general procedure 4, starting from Fe powder (92 mg, 1.64 mmol), calcium chloride (61 mg, 0.55 mmol), 3-{2-[2-(2-bromophenyl)pyrrolidin-1-yl]-2-oxoethyl}-1-[(1-methyl-1H-1,2,3-triazol-4-yl) methyl]-1-[(4-nitrophenyl)methyl] urea (305 mg, 0.55 mmol), in Ethanol/Water (8 mL, 6:2). The resultant oil was dissolved in a small amount of ethanol, to which 1.25 M HCl in ethanol was added. Evaporation of the solvent produced the title compound as an orange solid 300 mg (97%). Mp: 201-205° C. LC-MS: Rt=5.3 min, m/z 527 [M+2H]$^+$. $^1$H NMR (500 MHz, DMSO-d$_6$) δ 10.33 (bs, 2H), 7.89 (s, 1H), 7.62-7.59 (m, 1H), 7.36-7.32 (m, 3H), 7.32-7.23 (m, 2H), 7.21-7.13 (m, 3H), 5.21 (dd, J=8.1, 2.4 Hz, 1H), 4.46 (s, 2H), 4.38 (s, 2H), 4.01-3.95 (m, 5H), 3.92-3.88 (m, 1H), 3.61 (qd, J=10.0, 7.1 Hz, 1H), 2.26 (tt, J=12.1, 8.2 Hz, 1H), 1.95 (dtt, J=11.0, 7.9, 4.0 Hz, 1H), 1.90-1.73 (m, 1H), 1.70 (ddd, J=12.6, 6.2, 3.0 Hz, 1H). $^{13}$C NMR (126 MHz, DMSO-d$_6$) δ 168.46, 157.93, 144.41, 142.40, 139.01, 133.47, 133.02, 130.86, 129.34 (2C), 127.95, 127.39, 124.66, 123.67 (2C), 121.84, 60.73, 56.48, 46.76, 43.41, 38.72, 36.80, 32.29, 23.34. ESI+(m/z): [M+H]$^+$ calculated for C$_{24}$H$_{28}$$^{79}$BrN$_7$O$_2$ (100.0%) 525.1488; found 525.1473 [M+H]$^+$; calculated for C$_{24}$H$_{28}$$^{81}$BrN$_7$O$_2$ (97.3%) 527.1467; found 527.1478 [M+H]$^+$ LC-MS purity: 99%

1-[(4-aminophenyl)methyl]-3-{2-[2-(2-bromophenyl)pyrrolidin-1-yl]-2-oxoethyl}-1-[(2-methyl-2H-1,2,3,4-tetrazol-5-yl)methyl]urea hydrochloride (4)

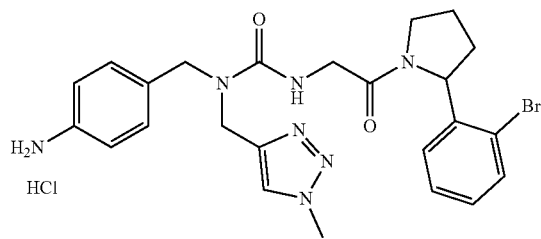 [SMILES: Cl ; Cn1cc(CN(Cc2ccc(N)cc2)C(=O)NCC(=O)N2CCCC2c2ccccc2Br)nn1]

The title compound was synthesized according to the general procedure 4, starting from Fe powder (64 mg, 1.15 mmol), calcium chloride (43 mg, 0.39 mmol), 3-{2-[2-(2-bromophenyl)pyrrolidin-1-yl]-2-oxoethyl}-1-[(2-methyl-2H-1,2,3,4-tetrazol-5-yl)methyl]-1-[(4-nitrophenyl)methyl] urea (215 mg, 0.39 mmol), in Ethanol/Water (8 mL, 6:2). The resultant oil was dissolved in a small amount of ethanol, to which 1.25 M HCl in ethanol was added. Evaporation of the solvent produced the title compound as an orange solid 120 mg (55%). Mp: 212-214° C. LC-MS: Rt=1.0 min, m/z 549 [M+Na]$^+$. $^1$H NMR (500 MHz, DMSO-d$_6$) δ 10.27 (bs, 2H), 7.62-7.58 (m, 1H), 7.36-7.24 (m, 5H), 7.16-7.10 (m, 3H), 5.19 (dt, J=8.3, 2.5 Hz, 1H), 4.46 (s, 2H), 4.38 (s, 2H), 4.30 (s, 3H), 4.01-3.95 (m, 2H), 3.85 (td, J=11.6, 10.4, 7.1 Hz, 1H), 3.59 (dtd, J=12.6, 6.9, 2.8 Hz, 1H), 2.26 (dtt, J=10.4, 8.0, 5.1 Hz, 1H), 1.94 (ddt, J=11.7, 7.0, 3.6 Hz, 1H), 1.79 (dtd, J=8.2, 5.4, 4.7, 2.6 Hz, 1H), 1.69 (ddt, J=11.8, 5.7, 2.6 Hz, 1H). $^{13}$C NMR (126 MHz, DMSO-d$_6$) δ 168.26, 162.76, 142.32, 133.03, 129.80, 129.03 (2C), 129.00, 128.59, 128.56, 127.97, 127.24, 123.45 (2C), 121.81, 60.71, 52.07, 46.67, 43.08, 36.25, 32.33, 31.25, 23.37. ESI+(m/z): [M+H]$^+$ calculated for C$_{23}$H$_{27}$$^{79}$BrN$_8$O$_2$ (100.0%) 526.1440; found 526.1470 [M+H]$^+$; calculated for C$_{23}$H$_{27}$$^{81}$BrN$_8$O$_2$ (97.3%) 528.1420; found 528.1428 [M+H]$^+$ LC-MS purity: 97%.

Ethyl 2-[4-({[(4-aminophenyl)methyl]({2-[2-(2-bromophenyl)pyrrolidin-1-yl]-2-oxoethyl}carbamoyl)amino}methyl)-1H-1,2,3-triazol-1-yl]acetate hydrochloride (5)

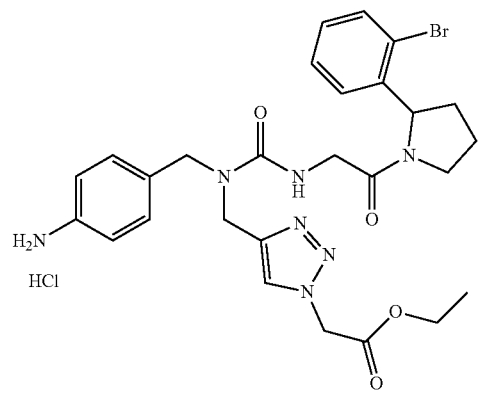 [SMILES: Cl ; CCOC(=O)Cn1cc(CN(Cc2ccc(N)cc2)C(=O)NCC(=O)N2CCCC2c2ccccc2Br)nn1]

A mixture of 1-[(4-aminophenyl)methyl]-3-{2-[2-(2-bromophenyl)pyrrolidin-1-yl]-2-oxoethyl}-1-(prop-2-yn-1-yl) urea hydrochloride (13) (250 mg, 0.5 mmol, 1 equiv), ethyl azidoacetate (25% solution in Ethanol, 0.4 mL, 0.6 mmol, 1.2 equiv), CuSO$_4$ (123 mg, 0.5 mmol, 1 equiv) and sodium ascorbate (196 mg, 1.0 mmol, 2 equiv) in EtOH/H$_2$O (20 mL, 1:1) was stirred at rt for 16 h. The reaction mixture was quenched with crushed ice and extracted with ethyl acetate (10 mL×3). The organic extracts were washed with brine solution (20 mL) and dried over anhydrous magnesium sulfate. The solvent was evaporated under reduced pressure to afford the desired compound. The resultant brown oil was dissolved in a small amount of ethanol, to which 1.25 M HCl in ethanol was added. Evaporation of the solvent produced the title compound as an orange solid 30 mg (10%). Mp: 186-190° C. LC-MS: Rt=5.3 min, m/z 598 [M+H]$^+$. $^1$H NMR (500 MHz, DMSO-d$_6$) δ 7.97 (t, J=9.6 Hz, 1H), 7.67 (dt, J=8.0, 1.5 Hz, 1H), 7.36-7.22 (m, 4H), 7.22-7.11 (m, 4H), 5.30-5.16 (m, 1H), 4.58-4.48 (m, 3H), 4.39 (d, J=11.2 Hz, 2H), 4.11-4.01 (m, 3H), 3.98 (d, J=3.0 Hz, 2H), 3.67-3.54 (m, 2H), 1.95 (ddt, J=12.5, 6.4, 3.1 Hz, 1H), 1.90-1.65 (m, 3H), 1.15 (t, J=7.1 Hz, 3H). $^{13}$C NMR (126 MHz, DMSO-d$_6$) δ 205.02, 163.93, 141.94, 140.54, 138.41, 138.20, 133.03, 132.88, 129.02 (2C), 128.83, 127.97, 127.62, 127.28, 123.57 (2C), 121.84, 60.76, 60.29, 48.95, 47.72, 46.76, 43.52, 42.80, 32.29, 23.36, 14.45. ESI+(m/z): [M+H]$^+$ calculated for C$_{27}$H$_{32}$$^{79}$BrN$_7$O$_4$ (100.0%) 597.1699; found 597.1670 [M+H]$^+$; calculated for C$_{27}$H$_{32}$$^{31}$BrN$_7$O$_4$ (97.3%) 599.1679; found 599.1668 [M+H]$^+$ LC-MS purity: 97%.

Ethyl 3-[4-({[(4-aminophenyl)methyl]({2-[2-(2-bromophenyl)pyrrolidin-1-yl]-2-oxoethyl}carbamoyl)amino}methyl)-1H-1,2,3-triazol-1-yl]propanoatehydrochloride (6)

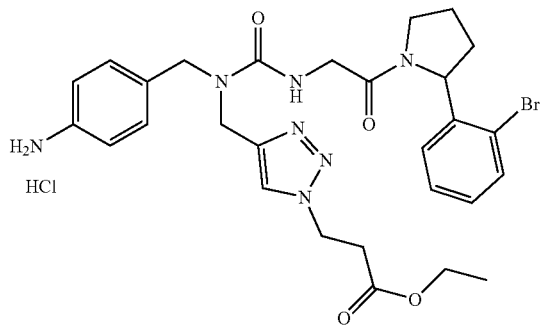 [SMILES: Cl ; CCOC(=O)CCn1cc(CN(Cc2ccc(N)cc2)C(=O)NCC(=O)N2CCCC2c2ccccc2Br)nn1]

A mixture of 1-[(4-aminophenyl)methyl]-3-{2-[2-(2-bromophenyl)pyrrolidin-1-yl]-2-oxoethyl}-1-(prop-2-yn-1-yl)urea hydrochloride (200 mg, 0.4 mmol), ethylazidopropionate (62 mg, 0.43 mmol), CuSO$_4$ (99 mg, 0.4 mmol) and sodium ascorbate (157 mg, 0.8 mmol) were stirred in EtOH/water (10 mL, 1:1) at RT for 16 h. Crushed ice was added and the mixture extracted with ethyl acetate. The combined organic extracts were dried over MgSO$_4$, filtered and the solvent removed in vacuo to a dark oil which was purified by flash column chromatography. Brown solid 51 mg, (20%) LC-MS: Rt=5.3 min, m/z 614 [M+2H]$^+$. $^1$H NMR (500 MHz, DMSO-d$_6$) δ 10.10 (s, 1H), 8.02-7.95 (m, 1H), 7.68 (dt, J=7.9, 1.5 Hz, 1H), 7.60 (ddd, J=7.9, 4.1, 1.3 Hz, 1H), 7.49-7.37 (m, 1H), 7.36-7.24 (m, 5H), 7.22-7.07 (m, 3H), 6.78-6.61 (m, 1H), 5.29-5.17 (m, 1H), 4.58-4.50 (m, 2H), 4.48-4.36 (m, 2H), 4.06 (q, J=7.1 Hz, 2H), 3.67-3.53 (m, 2H), 2.98-2.85 (m, 3H), 2.32-2.21 (m, 1H), 2.00-1.58 (m, 4H), 1.20-1.08 (m, 4H). $^{13}$C NMR (126 MHz, DMSO-ds) δ 170.70, 168.26, 157.93, 144.27, 142.42, 133.04, 129.05 (2C), 127.95, 127.29 (2C), 124.03, 123.37, 121.85, 60.77, 60.71, 48.92, 47.72, 46.76, 45.66, 43.50, 41.34, 35.41, 34.43, 32.29, 23.35, 21.28, 14.46.

1-[(4-aminophenyl)methyl]-3-{2-[(2S)-2-(2-bromophenyl)pyrrolidin-1-yl]-2-oxoethyl}-1-[(1-methyl-1H-1,2,3-triazol-4-yl)methyl]urea hydrochloride (7)

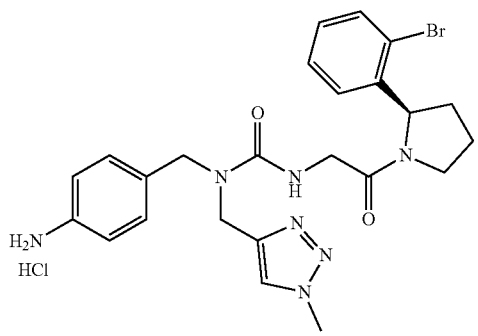 [SMILES: Cl ; Cn1cc(CN(Cc2ccc(N)cc2)C(=O)NCC(=O)N2CCC[C@@H]2c2ccccc2Br)nn1]

The title compound was synthesized according to the general procedure 4, starting from Fe powder (32 mg, 0.6 mmol), calcium chloride (21 mg, 0.20 mmol), 3-{2-[(2S)-2-(2-bromophenyl)pyrrolidin-1-yl]-2-oxoethyl}-1-[(1-methyl-1H-1,2,3-triazol-4-yl)methyl]-1-[(4-nitrophenyl)methyl]urea (105 mg, 0.19 mmol), in Ethanol/Water (8 mL, 6:2). The resultant oil was dissolved in a small amount of ethanol, to which 1.25 M HCl in ethanol was added. Evaporation of the solvent produced the title compound as an orange solid 50 mg (47%) αD=+1.24. LC-MS: Rt=5.3 min, m/z 526 [M+H]$^+$. $^1$H NMR (500 MHz, DMSO-d$_6$) δ 10.12 (s, 1H), 8.44 (s, 1H), 8.01-7.78 (m, 1H), 7.81-7.66 (m, 1H), 7.66-7.52 (m, 1H), 7.54-7.47 (m, 1H), 7.45-7.37 (m, 2H), 7.36-7.24 (m, 2H), 6.79 (d, J=8.5 Hz, 2H), 5.38-4.65 (m, 2H), 4.61-4.12 (m, 2H), 4.45 (s, 3H), 4.11-3.90 (m, 3H), 3.79-3.48 (m, 2H), 2.06-1.60 (m, 2H). $^{13}$C NMR (126 MHz, DMSO-d$_6$) δ 157.95, 144.45, 142.42, 136.10, 134.44, 133.04, 131.77, 129.08 (2C), 128.64, 127.96 (2C), 127.30, 124.64, 123.38, 63.45, 60.74, 56.48, 48.96, 36.70, 32.29, 23.35, 21.21.

1-[(4-aminophenyl)methyl]-3-{2-[2-(2-chlorophenyl)pyrrolidin-1-yl]-2-oxoethyl}-1-[(1-methyl-1H-1,2,3-triazol-4-yl)methyl]urea hydrochloride (8)

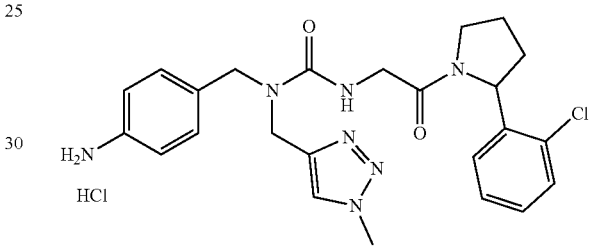

The title compound was synthesized according to general procedure 4, starting from Fe powder (90 mg, 1.61 mmol), calcium chloride (66 mg, 0.6 mmol), 3-{2-[2-(2-chlorophenyl)pyrrolidin-1-yl]-2-oxoethyl}-1-[(1-methyl-1H-1,2,3-triazol-4-yl) methyl]-1-[(4-nitrophenyl)methyl]urea (192 mg, 0.38 mmol), in Ethanol/Water (10 mL, 3:1). The resultant oil was dissolved in a small amount of ethanol, to which 1.25 M HCl in ethanol was added. Evaporation of the solvent produced the title compound as an orange solid. 30 mg (15%). LC-MS: Rt=5.2 min, m/z 482 [M+2H]$^+$. $^1$H NMR (500 MHz, DMSO-d$_6$) δ 10.38 (s, 1H), 7.99-7.83 (m, 2H), 7.54-7.37 (m, 3H), 7.31-7.22 (m, 2H), 7.22-7.12 (m, 1H), 5.38-5.20 (m, 1H), 5.17-4.80 (s, 5H), 4.65-4.30 (m, 3H), 4.05-3.92 (m, 3H), 3.80-3.52 (m, 2H), 2.37-2.16 (m, 2H), 1.99-1.61 (m, 3H). $^{13}$C NMR (126 MHz, DMSO-d$_6$) δ 168.50, 158.00, 144.47, 140.92, 131.39, 129.80 (2C), 129.03 (2C), 127.43, 127.19, 125.63, 124.75, 123.67, 58.53, 57.98, 48.96, 46.64, 43.52, 37.02, 36.68, 34.41, 32.14, 23.47.

Protein Expression and Purification

The plasmids of HisCypA, HisCypB and HisCypD were provided by the Edinburgh Protein Production Facility (EPPF). Protein expression and purification protocols were slightly modified from Wear et al. for their usage in ITC and X-ray studies (Wear 2017).

Recombinant Cyclophilins (Cyps) were produced in C41 BL21(DH3) E. coli cell lines (Lucigen, Middleton, Wis., USA). Briefly, 1 μL of the stock plasmids were added to the competent cells, left on ice for about half an hour and after a two-minute heat shock at 42° C. were incubated by shaking (250 rpm) in SOC media (500 μL) at 37° C. for 45 minutes. They were left overnight to colonize in agar plates (100 μL/plate) containing carbenicillin (100 μg mol$^{-1}$). After this a single colony was picked and grown for six hours in LB media. Subsequently, 20% v/v glycerol was added and these glycerol stocks were used in future reference.

A 100 mL pre-culture was left overnight in LB media using a glycerol stock and carbenicillin as antibiotics (100 µg mol$^{-1}$). The cultures were centrifuged for five minutes at 1,500 g and new 500 mL cultures were made by transferring the cell pellets, adding carbenicillin and incubating by shaking (250 rpm) until $OD_{600}$ 0.6-0.8 at 37° C. and then induced at 30° C. with 0.5 mM IPTG for four hours. Finally, the cultures were pelleted by centrifugation at 8,000 g for 20 minutes at 4° C. prior to cell lysis.

All purifications were performed on ÄKTA Pure (GE Healthcare) equipment at 4° C. Prior to purification cell pellets were lysed using protease inhibitors (Roche) in loading buffer (20 mM phosphate, 300 mM NaCl, 20 mM imidazole, pH 7.4) by a double passage on a Constant Systems Cell Disruptor (1.1 kW TS Benchtop) at 22 kpsi followed by one-hour centrifugation at 4° C. (55,000 g). A two-step purification protocol was used in all cases, i.e. Immobilized Metal Ion Affinity Chromatography (IMAC) and Size Exclusion Chromatography (SEC) using the HiTrap IMAC FF 5 mL and the HiLoad Superdex 75 µg 16/60 columns, respectively. The buffer used in the SEC purification step was similar to the ITC buffer and for the IMAC elution 20 mM phosphate, 300 mM NaCl, 500 mM imidazole, pH 7.4. Protein His-Tag was cleaved for further use of the protein in ITC and X-ray studies, whereas for the SPR experiments the protein was uncleaved. Proteins were desalted to cleavage buffer (100 mM Tris, 100 mM NaCl, pH 7.5) using a HiPrep 26/10 desalting column prior to the addition of TEV protease (200 ng TEV/40 µg protein). Samples were left incubating at 30° C. for about four hours and the cleaved His-tag was removed by IMAC. At the end of each purification the purity of the fractions was tested by using precast gels (Biorad®) in Tris/Glycine/SDS, pH 8.3 buffer. The molecular weights of HisCypA and free CypA are 20.893 and 18.069 kDa, respectively. Protein concentration was determined by measuring the absorbance at 280 nm and the extinction coefficients 14440 and 8480 M$^{-1}$ cm', respectively.

Isothermal Titration Calorimetry (ITC)

All ITC experiments for the ester series compounds were carried out at 25° C. on a MicroCal Auto iTC200 (GE Healthcare) instrument. The buffer used in the titrations of the compounds belonging to the ester series was 50 mM phosphate buffer, pH 6.5 and the concentration of DMSO was 2% v/v for all the compounds, unless otherwise stated in Table 51. Final compound solutions were heated to 65° C. and/or sonicated prior to the experiment. Each experiment consisted of an initial injection of 0.4 µL followed by nineteen 2 µL injections and in most of cases for these compounds, the "continue injections" protocol was used leaving the cell intact and performing a second series of titrations using the above protocol to achieve saturation. Control experiments were performed, where each compound was titrated into buffer and when small amount of heat was detected due to heat of dilution, it was subtracted when processing the data using a linear fit method. In all cases the first injection was omitted from the data processing. All data were analysed using the MicroCal PEAQ-ITC Analysis software. Because some compounds have affinity that lie in the low-mid micromolar range and the c value (Wiseman constant) is very small, a fixed stoichiometry to 1 was applied during the non-linear regression of the raw data for fitting the data (Tellinghuisen, J., Isothermal titration calorimetry at very low c. *Analytical biochemistry*, 373 (2), 395-7, 2008). Control runs on literature compounds were run as a control at the end of each experiment to verify that CypA remained active during the duration of the experiment.

Compound belonging to the arryl-pyrrolidine series, were tested using a reverse titration method or a reverse titration using a competition-based method as previously described with CsA (Low-Affinity Binding Determined by Titration calorimetry Using a High-Affinity Coupling Ligand: A Thermodynamic Study of Ligand Binding to Protein Tyrosine Phosphatase. Zhang Y, Zhang Z. *Analytical biochemistry*, 261, 139-148, 1998). The buffer used for these titrations was: PBS, 0.05% v/v P20 surfactant, 50 µM EDTA in presence of 2% v/v EtOH and the pH was set to 7.4. For the reverse competitive titrations Cyclophilin A (60 µM) was titrated into 4 µM CsA in presence of 10 µM compound in cell using a 15-injection protocol. A control experiment comprising of a titration of 60 µM CsA into 4 µM CsA using the same instrument parameters was performed.

Surface Plasmon Resonance (SPR)

SPR measurements were performed on a BIAcore T200 instrument (GE Healthcare). Ni$^{2+}$-nitrilotriacetic acid (NTA) sensor chips, 1-ethyl-3-(3-diaminopropyl) carbodiimide hydrochloride (EDC) and Nhydroxysuccinimide (NHS) were purchased from GE Healthcare.

Pure His-cyclophilins were immobilized and covalently stabilized on the NTA sensor chip according to the protocol described in Thermo-kinetic analysis space expansion for cyclophilin-ligand interactions—identification of a new nonpeptide inhibitor using Biacore T200. Wear, M. A.; Nowicki, M. W.; Blackburn, E. A.; McNae, I. W.; Walkinshaw, M. D., *FEBS open bio* 7 (4), 533-549 (2017), using 200 nM concentrations of each protein, in Running Buffer (PBS, pH 7.4; 0.05% surfactant P20, 2% v/v ethanol; 50 µM EDTA), at 30 µl min$^{-1}$ with 60 second contact times on the activated NTA surfaces. This gave signals of 1,921 RU for His-CypA, 1932 RU for His-CypB and 1,397 RU for His-CypD. Specific surface protein activity was assayed by passing saturating amounts of CsA (2 µM) in Running Buffer over these surfaces; values of 94.1%, 95.5% and 95.6% activity were obtained for His-CypA, -B and -D, respectively.

Single cycle kinetic titration binding experiments were performed using SPR in triplicate at 25° C. 3-fold dilution concentration series of CsA, ranging from 2.45 nM to 200 nM, in Running Buffer (PBS, pH 7.4, 50 µM mM EDTA; 0.05% v/v surfactant P20; 2% v/v ethanol), were injected over the sensor surface, at 100 µl·min$^{-1}$ with a 90 s contact time and a 90 s dissociation time. The sensor surface was regenerated between experiments by dissociating any formed complex in running buffer for at least 1,200 seconds. The apparent on-rate (k+) and off-rate (k−) constants and the equilibrium dissociation constant ($K_d$) were calculated from reference corrected sensorgrams by global fitting of a 1:1 binding model, including a mass transport term, using analysis software (v. 2.02, GE Healthcare) provided with the BIAcore T200 instrument.

Kinetic titration binding experiments were performed in triplicate at 25° C. 2-fold dilution concentration series of the compounds, ranging from 0.0195 µM to 20 µM, in Running Buffer (PBS, pH 7.4, 50 µM mM EDTA; 0.05% v/v surfactant P20; 2% v/v ethanol), were injected over the sensor surface, at 100 µl·min$^{-1}$ with a 15 s contact time and a 600 s dissociation time. The sensor surface was regenerated between experiments by dissociating any formed complex in running buffer for at least a further 600 seconds. The apparent on-rate (k+) and off-rate (k−) constants and the equilibrium dissociation constant ($K_d$) were calculated from reference corrected sensorgrams by global fitting of a 1:1 binding model, including a mass transport term, using analysis software (v. 2.02, GE Healthcare) provided with the BIAcore T200 instrument.

X-Ray Diffraction Experiments

Purified and his-tag-cleaved CypA was buffer-exchanged into PBS and concentrated to ~29 mg ml$^{-1}$. For crystallisation 1 μL of protein was mixed with an equal volume of the well solution, consisting of 100 mM Tris-HCl pH8.0 and 20-22% v/v PEG 8000, and crystal formation came about after equilibration overnight in 6° C. by vapour diffusion using the hanging drop method over 1 mL of the same well solution. Apo CypA crystals were soaked overnight into different ligand solution consisting of 100 mM Tris-HCl pH 8.0, 35% w/v PEG 8000, 5% v/v Glycerol, 5% v/v DMSO and 5 mM ligand, before flash frozen into liquid nitrogen. X-ray data were collected at the Diamond synchrotron-radiation facility in Oxford-shire, England at 100K. Structures were solved by molecular replacement using DIMPLE from the CCP4i suite. Modelled structures were visualised and manually adjusted as needed using Coot10 and further refined using REFMAC5 from CCP4i.

Cell Assays

Dulbecco's Modified Eagle's Medium (DMEM, with high glucose, sodium bicarbonate and L-glutamine), myo-inositol and folic acid were purchased from Sigma-Aldrich, Alpha MEM without ribonucleosides and deoxyribonucleosides, fetal bovine serum (FBS), heat-inactivated FBS heat-inactivated horse serum, β-mercaptoethanol and Ready-To-Use Geltrex were purchased from Life Technologies, and recombinant human IL-2 was purchased from Peprotech. Draq 7 was purchased from New England Biolabs and NucView 488 was purchased from Biotium. 384-well micro-clear tissue culture-treated plates for microscopy were purchased from Greiner Bio-One. Cyclophilin A antibody (rat polyclonal), cyclophilin B antibody (rabbit monoclonal) and GAPDH antibody (rabbit monoclonal) were purchased from New England Biolabs. Cyclophilin D antibody (mouse monoclonal) and mammalian protein extraction reagent (M-PER) was purchased from Thermo-Fisher Scientific. Complete EDTA-free protease inhibitor and phosSTOP phosphatase inhibitor were purchased from Roche. IRDye 800CW goat anti-rabbit, IRDye 800CW goat anti-mouse antibodies and IRDye 680RD were purchased from Li-Cor BioSciences. 4-15% mini protean TGX stain-free gels, 10× tris/glycine/SDS PAGE buffer and Transblot Turbo Midi nitrocellulose transfer packs were purchased from Bio-Rad Laboratories.

The tumorigenic, breast, epithelial adenocarcinoma cell lines MDA-MB-231_NLG, MDA-MB-231_NLR, MDA-MB-468_NLR, SKBR3-NLR, MCF7_NLR and the normal, lung fibroblast cell line, IMR90 were cultured as adherent monolayers in DMEM with 10% volume FBS in an atmosphere with 5% $CO_2$ and 95% humidity and were routinely sub-cultured upon reaching 80-90% confluence. The natural killer cell line NK92 was cultured in suspension in alpha MEM medium with 12.5% volume heat inactivated fetal bovine serum, 12.5% volume heat-inactivated horse serum, 0.02 mM folic acid, 0.1 mM 3-mercaptoethanol, 0.2 mM myo-inositol and 200 U/mL IL-2. The latter medium with 2000 U/mL IL-2 was used for NK92 cell killing assays. MDA-MB-231 NLG and MDA-MB-468_NLR cells are a variant of MDA-MB-231 cells, expressing nuclear-restricted green fluorescent protein or nuclear-restricted mKate2 fluorescent protein respectively while MDA-MB-468_NLR, SKBR3_NLR and MCF7_NLR are, respectively, variants of MDA-MB-468, SKBR3 and MCF7 cells expressing nuclear-restricted mKate2 fluorescent protein; the cell lines with nuclear-restricted fluorescent protein were produced by stable transduction of cells with NucLight Green lentivirus or Nuclight Red lentivirus (Essen Bioscience), following the manufacturer's protocol.

To determine the direct effect of the compounds on cell proliferation, cells were seeded at a density of 500 cells per well in cell culture medium in 384-well cell culture plates and allowed to adhere overnight (about 16 hours), incubated in a humidified atmosphere with 5% $CO_2$. Subsequently, cell culture medium was refreshed, supplemented with Draq 7 (3 μM final concentration) and test compound at the indicated concentrations with three wells being treated for each condition tested. Cells were then returned to the cell culture incubator and imaged with a 10× objective every 3 hours for 120 hours using an IncuCyte ZOOM microscope from Essen Bioscience.

Using the IncuCyte ZOOM software, custom image analysis procedures were developed and applied for each cell line to determine cell confluency, cell number and number of dead cells over the time course of the experiment. Phase contrast was used to determine relative area of each image occupied by cells (confluency), while green nuclear counts were used to determine number of MDA-MB-231_NLG cells and red nuclear counts were used to determine number of dead (Draq7-positive) cells.

Cell viability was determined relative to vehicle-treated (0.1% DMSO) controls using the $GI_{50}$ method established by the National Cancer Institute with $GI_{50}$ values (concentration of compound causing 50% growth inhibition) being determined by fitting non-linear regression curves to the data and extrapolating the required values using GraphPad Prism 6. Statistical analyses in cell viability assays to compare the effect of compound treatment to treatment with vehicle were performed using GraphPad Prism 6 (2-way ANOVA with Bonferroni correction post hoc).

To determine and quantify the expression of cyclophilins in the cell lines, cells were lysed with ice-cold MPER supplemented with protease and phosphatase inhibitor cocktails. Clarified lysates were resolved on 4-15% Tris-glycine gels by SDS-PAGE and total protein transferred to nitrocellulose membrane. Membranes were blocked with Li-Cor Buffer, probed with appropriate primary antibodies overnight, followed by washing and probing with appropriate fluorescence-conjugated secondary antibodies. Membranes were imaged and fluorescence intensity on the membranes recorded using the Li-Cor Odyssey CLx imager.

To determine the effect of the compounds on immune cell killing of target cancer cells, cancer cells (MDA-MB-231_NLR, MDA-MB-468_NLR, SKBR3_NLR or MCF7_NLR) were seeded at a density of 250 cells per well in NK92 cell culture medium with 2000 U/mL IL2, supplemented with 2.5 μM NucView 488 in GelTrex-coated 384-well cell culture plates. NK92 cells were then added at a density of 1000 cells per well and 10 μM test compound was added. Cells were imaged with a 10× objective every 3 hours for 120 hours using an IncuCyte ZOOM microscope from Essen Bioscience.

Using the IncuCyte ZOOM software, custom image analysis procedures were developed and applied for each cell line to determine cell number (red nuclei) and number of apoptotic cells (NucView 488-positive nuclei with co-localized red and green fluorescent signal) over the time course of the experiment. Apoptotic fraction of the population (number of nuclei with co-localized red and green fluorescence divided by total number of red nuclei in the population) and fold increase in number of red nuclei were determined at various time points.

Cyps Binding

FIG. 1A summarises the mode of binding of certain prior-art urea small molecule Cyp inhibitors. In the so-called 'type-I binding mode' the compounds may interact with the Abu and Pro pockets of the Cyps surfaces. In the so called novel 'type-II binding mode' depicted in FIG. 1B the compounds may interact with the Abu, Pro and 3 o'clock pockets of the Cyps surfaces. A type-II binding mode compound may be obtained by replacement of the shaded H atom in a type-I binding mode compound with a suitably chosen R group to create tri-vector Cyclophilin inhibitor derivatives. This modification is not obvious given the prior-art because the vector between the nitrogen atom bonded to the shaded H atom and the shaded H atom points away from the 3 o'clock. Thus conversion from a type-I binding mode to a type-II binding mode involves a 180 degree flip of the urea moiety to position the R group towards the 3 o'clock pocket. Only certain non-obvious R groups are able to accommodate this urea flip. FIG. 1C depicts a crystal structure of CypA in complex with a prior-art compound (R=H) showing that the compound does not access the 3 o'clock pocket. FIG. 1D depicts the crystal structure of CypA in complex with a novel tri-vector derivative (R=Et) that does not adopt a type-II binding mode. FIG. 1E and FIG. 1F depict crystal structures of CypA in complex with novel tri-vector derivatives (R=tetrazolyl-methyl) that adopt a type-II binding mode enabling interactions between their R groups and the 3 o'clock pocket.

Table 1 shows that tri-vector derivatives show a range of binding constants measured by isothermal titration calorimetry experiments (ITC) consistent with CypA inhibition with $K_d$ values ranging from high micromolar to mid-nanomolar.

Table 1 also shows that selected tri-vector derivatives show a range of binding constants measured by surface plasmon resonance (SPR) experiments consistent with CypA, CypB and CypD inhibition, with $K_d$ values ranging from low micromolar to mid-nanomolar. In the case of CypD, some tri-vector derivatives show a potency that approaches that of the drug Cyclosporine A. For comparison the most potent literature compounds (Fragment-based discovery of a new family of non-peptidic small-molecule cyclophilin inhibitors with potent antiviral activities. Ahmed-Belkacem A, Colliandre L, Ahnou N, Nevers Q, Gelin M, Bessin Y, Brillet R, Cala O, Douguet D, Bourguet W, Krimm I, Pawlotsky J Ml, Guichou J F. *Nature Communications* 7: 12777, 2016) are reported to have $IC_{50}$ values of ca. 0.2 micromolar against CypD. Thus some of the present tri-vector derivatives are more potent than the previous generation of small molecule Cyp inhibitors. The data in Table 1 also shows that some of the tri-vector derivatives show up to 25-fold selectivity for CypA, B or D, which is over 10 times greater than what is measured for the drug Cyclosporine A or other small molecule inhibitors Table 1 shows that some of the tri-vector derivatives show superior growth inhibition 50 (GI50) values over the drug Cyclosporine A in growth inhibition experiments against a triple-negative breast cancer cell line that has previously been reported to be sensitive to Cyclosporine A (Prolyl isomerase cyclophilin A regulation of Janus-activated kinase 2 and the progression of human breast cancer. Zheng J, Koblinski J E, Dutson L V, Feeney Y B, Clevenger C V. *Cancer Res.* 68(19):7769-78, 2008). Table 1 shows that the tri-vector derivatives inhibit growth without causing cell death in the MDA-MB-231 cancer cell line and the non-cancerous control cell line IMR-90, whereas Cyclosporine A causes cell death in both cases. Western Blotting experiments confirmed that both cell lines express CypA, CypB and CypD.

Table 2 shows that the tri-vector derivatives are not toxic to NK92 cells whereas CsA shows pronounced toxicity, and that the combination of tri-vector derivatives with NK92 cells is more effective at reducing proliferation of MDA-MB-231 cancer cell lines than the combination of CsA with NK92 cells. This shows that immunotherapies based on combination of novel tri-vector cyclophilin ligands with NK cells may be more effective than immunotherapies based on combination of CsA with NK cells.

Table 1 summarises binding and inhibition experiments carried out on tri-vector derivative. Table 2 summarises results from additional cell assay experiments carried out on compounds 1 and 4.

Altogether the data in Table 1, Table 2 and FIG. 1 confirm the usefulness of tri-vector Cyclophilin ligands as potent and selective Cyclophilin inhibitors with reduced toxicity over other scaffolds such as the drug Cyclosporine A.

TABLE 1

Summary of binding and inhibition activity.
All figures are in micromolar. CsA: Cyclosporine A.

| Compound | CypA Kd (ITC) | CypA X-ray co-crystal | CypA Kd (SPR) | CypB Kd (SPR) | CypD Kd (SPR) | GI50 MDA-MB-231 cells | Toxicity MDA-MB-231 @10 µM | Toxicity IMR-90 @10 µM |
|---|---|---|---|---|---|---|---|---|
| CSA | 0.011 ± 0.001 | Y | 0.024 ± 0.006 | 0.010 ± 0.003 | 0.019 ± 0.005 | 6.2 ± 0.8 | Y | Y |
| 1 | 2 ± 1 | Y | 3.2 ± 1.3 | 1.4 ± 0.4 | 0.2 ± 0.1 | 5.1 ± 0.9 | N | N |
| 2 | ~1 | Y | 1.7 ± 0.8 | 0.9 ± 0.3 | 0.06 ± 0.03 | ND | N | N |
| 3 | ~1 | Y | 1.7 ± 1.0 | 0.3 ± 0.2 | 2.9 ± 1.2 | NT | NT | NT |
| 4 | 0.8 ± 0.1 | Y | 0.6 ± 0.4 | 0.2 ± 0.1 | 0.07 ± 0.03 | 2.8 ± 0.9 | N | N |
| 5 | ~3 | N | 4.3 ± 1.0 | 1.9 ± 0.9 | 1.0 ± 0.4 | ND | NT | NT |
| 6 | 0.30 ± 0.08 | N | NT | NT | NT | NT | NT | NT |
| 7 | 3.0 ± 0.5 | Y | 4.5 ± 1.0 | 0.7 ± 0.4 | 4.7 ± 2.9 | NT | NT | NT |
| 8 | 1.1 ± 0.4 | N | NT | NT | NT | NT | NT | NT |
| 9 | 35 ± 5 | Y | NT | NT | NT | NT | NT | NT |
| 10 | ~25 | N | NT | NT | NT | NT | NT | NT |
| 11 | ~10 | Y | NT | NT | NT | NT | NT | NT |
| 12 | 200 ± 5 | Y | NT | NT | NT | NT | NT | NT |

TABLE 1-continued

Summary of binding and inhibition activity.
All figures are in micromolar. CsA: Cyclosporine A.

| Compound | CypA Kd (ITC) | CypA X-ray co-crystal | CypA Kd (SPR) | CypB Kd (SPR) | CypD Kd (SPR) | GI50 MDA-MB-231 cells | Toxicity MDA-MB-231 @10 μM | Toxicity IMR-90 @10 μM |
|---|---|---|---|---|---|---|---|---|
| 13 | 990 ± 20 | Y | NT | NT | NT | NT | NT | NT |
| 14 | 139 ± 4 | N | NT | NT | NT | NT | NT | NT |
| 15 | 35 ± 5 | Y | NT | NT | NT | NT | NT | NT |
| 16 | 266 ± 3 | Y | NT | NT | NT | NT | NT | NT |
| 17 | ND | Y | NT | NT | NT | NT | NT | NT |
| 18 | 135 ± 6 | Y | NT | NT | NT | NT | NT | NT |
| 19 | 184 ± 13 | Y | NT | NT | NT | NT | NT | NT |
| 20 | >600 | Y | NT | NT | NT | NT | NT | NT |
| 21 | ND | Y | NT | NT | NT | NT | NT | NT |
| 22 | >1000 | Y | NT | NT | NT | NT | NT | NT |
| 23 | 700 ± 235 | N | NT | NT | NT | NT | NT | NT |

NT Not tested
ND Not determined
Y observed in cocrystal or evidence of dose dependent cytotoxicity
N not observed in cocrystal or no evidence of dose dependent cytotoxicity

TABLE 2

Summary of anti-proliferative activity

| Compound | Fold increase MDA-MB-231 cells in presence of NK92 cells after 72 h @ 10 μM | Fold increase in NK92 cells after 72 h @ 10 μM | Apoptotic fraction of the MDA-MB-231 population in the presence of NK92 cells after 72 h @ 10 μM |
|---|---|---|---|
| DMSO | 2.6 ± 0.4 | 4.1 ± 0.3 | 0.56 ± 0.03 |
| CsA | 3.0 ± 0.6 | 2.5 ± 0.3 | 0.38 ± 0.01 |
| 1 | 2.0 ± 0.3 | 4.3 ± 0.7 | 0.64 ± 0.03 |
| 4 | 1.0 ± 0.4 | 4.7 ± 0.5 | 0.58 ± 0.03 |

The invention claimed is:

1. A compound of formula I,

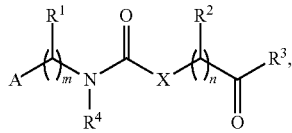
(I)

or a pharmaceutically acceptable salt thereof, wherein:

$R^1$ and $R^2$ are each independently selected from the group consisting of —R, -haloalkyl, -hydroxyalkyl, —OR, —C(O)R, —CO2R, —C(O)N(R)2, —NRC(O)R, and —N(R)2; wherein $R^2$ may also be a sulphide;

each R is independently hydrogen, $C_{1-6}$ aliphatic, $C_{3-10}$ aryl, a 3-8 membered saturated or partially unsaturated carbocyclic ring, a 3-7 membered heterocyclic ring having 1-4 heteroatoms independently selected from nitrogen, oxygen, sulphur, or a 5-6 membered monocyclic heteroaryl ring having 1-4 heteroatoms independently selected from nitrogen, oxygen, or sulphur;

$R^3$ is selected from the group consisting of —OEt, and

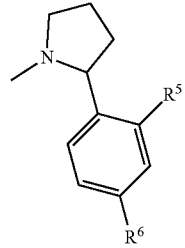

wherein $R^5$ and $R^6$ are independently selected from the group consisting of H, halide, methoxy, thiomethyl, morpholine and trifluoromethyl;

$R^4$ is selected from the group consisting of $C_{1-6}$-alkyl-, and $R^{4.1}$—$CH_2$— wherein, $R^{4.1}$ is $C_{3-6}$-cycloalkyl;

X is $CH_2$ nitrogen NH;

wherein A is selected from the group consisting of

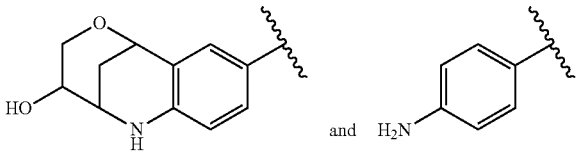 [SMILES: *c1ccc2c(c1)C1CC(N2)C(O)CO1 ; "and" ; *c1ccc(N)cc1]

and m is 1 or 2; and n is 1 or 2.

2. The compound or the pharmaceutical salt thereof according to claim 1, wherein $R^3$ is —OEt.

3. The compound according to claim 1, wherein R³ is

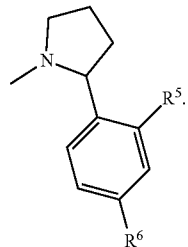

4. The compound according to claim 3, wherein R⁶ is H and R⁵ is selected from the group consisting of —Br, —Cl, —OMe, —SMe, —CF₃, -morpholine and —H.

5. The compound according to claim 1, wherein R¹ and R² are —H, and X is NH.

6. The compound according to claim 2 selected from the group consisting of

12

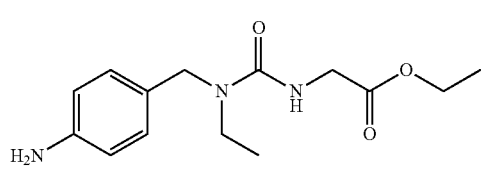

15

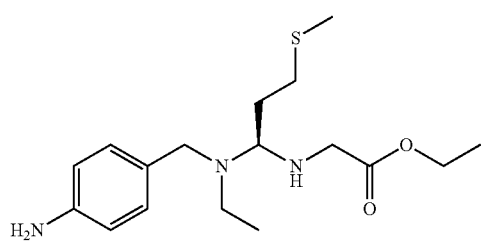

16

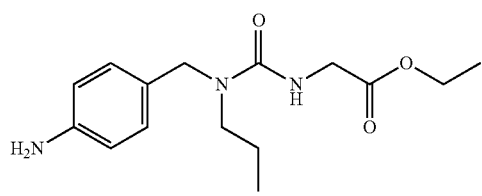

17

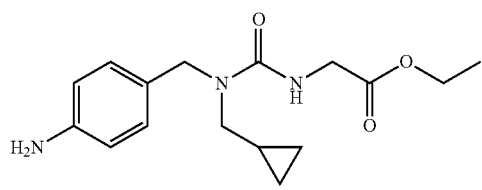

23

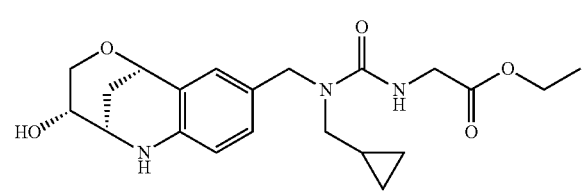

or a pharmaceutically acceptable salt thereof.

7. The compound according to claim 4 selected from the group consisting of

9

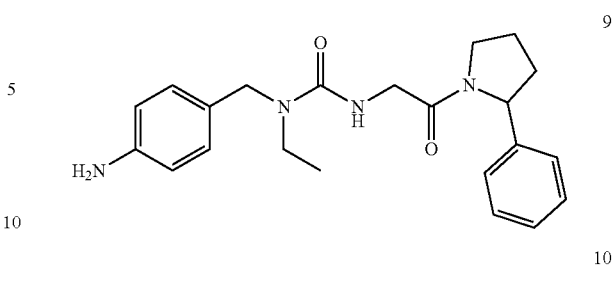

10

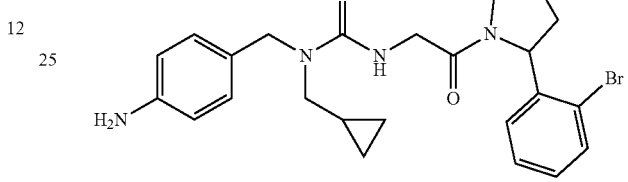

11

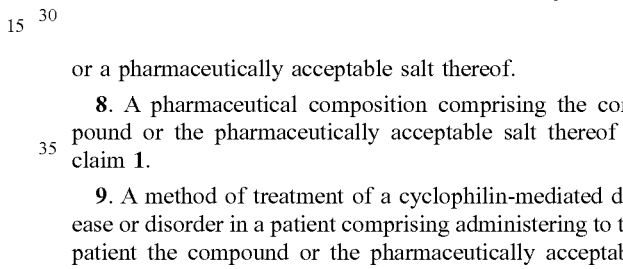

or a pharmaceutically acceptable salt thereof.

8. A pharmaceutical composition comprising the compound or the pharmaceutically acceptable salt thereof of claim 1.

9. A method of treatment of a cyclophilin-mediated disease or disorder in a patient comprising administering to the patient the compound or the pharmaceutically acceptable salt thereof of claim 1.

10. The method of treatment according to claim 9 wherein the disease or disorder is selected from the group consisting of fibrosis of the kidney, liver, lung or pancreas, cardiac failure, viral infections, inflammation, cancer, Alzheimer's disease, Parkinson's disease, Amyotrophic Lateral Sclerosis (ALS), Dementia, Multiple Sclerosis, and Huntington's disease.

11. The method of treatment according to claim 9 wherein the disease or disorder is treatable using immunotherapy.

12. A compound selected from a group consisting of

3

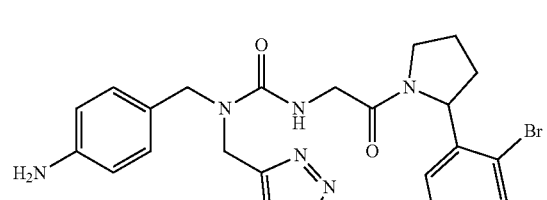

4
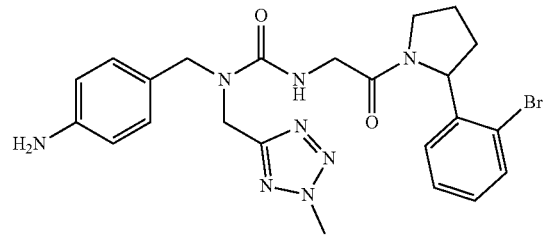

5
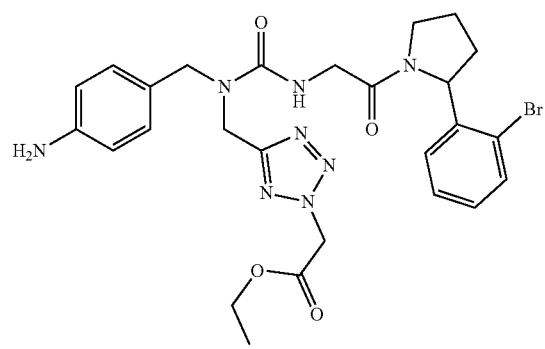

6
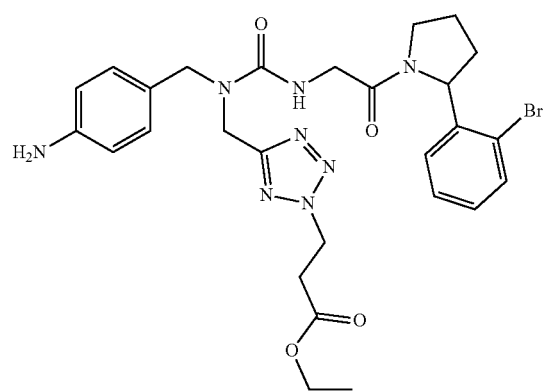

7
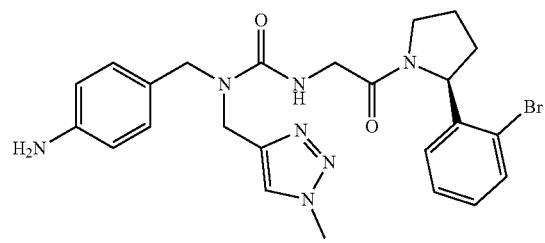

8
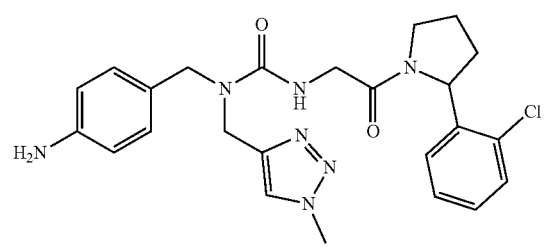

14
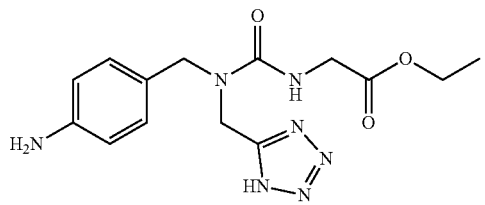

18
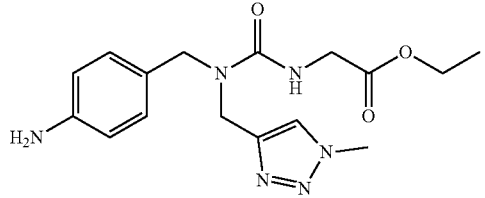

19
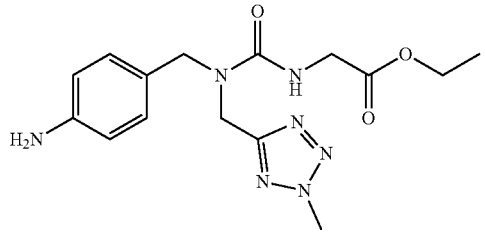

20
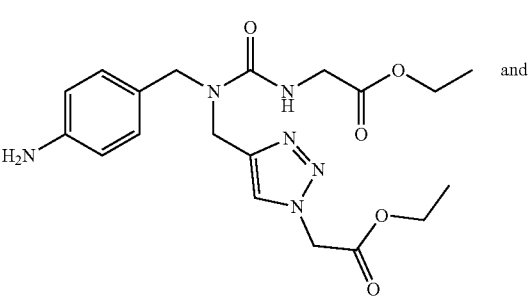
and

21
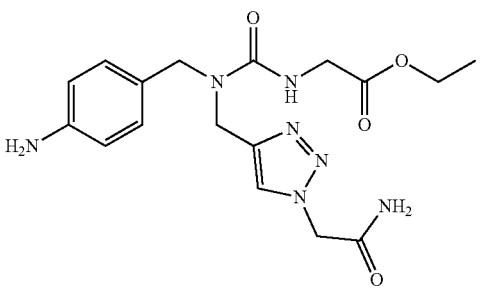, or a pharmaceutically acceptable salt thereof.

13. A pharmaceutical composition comprising the compound or the pharmaceutically acceptable salt thereof of claim 12.

14. A method of treatment of a cyclophilin-mediated disease or disorder in a patient comprising administering to the patient the compound or the pharmaceutically acceptable salt thereof of claim 12.

15. The method of treatment according to claim 14 wherein the disease or disorder is selected from the group consisting of fibrosis of the kidney, liver, lung or pancreas, cardiac failure, viral infections, inflammation, cancer, Alzheimer's disease, Parkinson's disease, Amyotrophic Lateral Sclerosis (ALS), Dementia, Multiple Sclerosis, and Huntington's disease.

16. The method of treatment according to claim 14 wherein the disease or disorder is treatable using immunotherapy.

\* \* \* \* \*